United States Patent
Lane et al.

(10) Patent No.: US 8,808,178 B2
(45) Date of Patent: Aug. 19, 2014

(54) ON DEMAND HELP/IN-SERVICE FOR A MEDICAL DEVICE

(75) Inventors: John A. Lane, Weedsport, NY (US); Suzanne Abate Gunter, Concord, NC (US); Alisa J. Robinson, Fayetteville, NY (US); James M. Robinson, Camillus, NY (US); Lari E. Shreffler, Jamesville, NY (US); Shawn C. St. Pierre, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1520 days.

(21) Appl. No.: 12/112,444

(22) Filed: Apr. 30, 2008

(65) Prior Publication Data
US 2009/0275805 A1  Nov. 5, 2009

(51) Int. Cl.
| | |
|---|---|
| *A61B 8/00* | (2006.01) |
| *G06F 9/44* | (2006.01) |
| *A61B 5/02* | (2006.01) |
| *A61B 5/0205* | (2006.01) |
| *A61B 5/024* | (2006.01) |
| *A61B 5/08* | (2006.01) |
| *A61B 5/00* | (2006.01) |
| *G06F 19/00* | (2011.01) |
| *G06F 9/00* | (2006.01) |
| *G01K 13/00* | (2006.01) |

(52) U.S. Cl.
CPC ........ *G06F 19/3406* (2013.01); *G06F 19/3487* (2013.01); *G06F 9/4446* (2013.01); *G01K 13/002* (2013.01); *A61B 5/02* (2013.01); *A61B 5/0205* (2013.01); *A61B 5/024* (2013.01); *A61B 5/08* (2013.01); *A61B 5/72* (2013.01); *A61B 5/7271* (2013.01); *A61B 5/74* (2013.01); *A61B 5/7425* (2013.01); *Y10S 128/92* (2013.01)
USPC .......... 600/300; 600/549; 600/529; 600/323; 600/324; 600/481; 374/100; 715/705; 715/709; 128/920

(58) Field of Classification Search
USPC ............... 600/300–301, 363–365, 373–374, 600/377–384, 386–394, 481–485, 500–503, 600/509, 515–519, 529–538, 549, 600/544–547; 128/200.24–200.29, 128/201.11–201.29, 202.11–202.29, 128/203.11–203.29, 204.11–204.29, 128/205.11–205, 920–925; 705/2–3
See application file for complete search history.

(56) References Cited

U.S. PATENT DOCUMENTS 4,879,999 A * 11/1989 Leiman et al. ........... 128/207.14
5,291,879 A *  3/1994 Babb et al. ............... 128/200.26
(Continued)

OTHER PUBLICATIONS

Thompson, J. E. et al in "Capnographic Waveforms in the Mechanically Ventilated Patient", Respiratory Care, Jan. 2005, vol. 50 No. 1, p. 100-109.*    (Continued)

*Primary Examiner* — Gary Jackson
*Assistant Examiner* — Marie Archer
(74) *Attorney, Agent, or Firm* — Hiscock & Barclay, LLP

(57) ABSTRACT

The invention is a medical monitor including an electronic circuit configured to receive a signal from the physiological sensor. A microcomputer configured to process the signal from the physiological sensor generates a value representative of the physiological parameter. The microcomputer is also configured to cause the medical monitor to display an in-service help screen on a display on the medical monitor in response to a detection of a predetermined number of out of range values of the physiological parameter. The microcomputer can also be configured to process a second signal from a second sensor representative of a second parameter and the microcomputer configured to cause the medical monitor to display an in-service help screen on a display on the medical monitor in response to a detection of a predetermined number of out of range values of the second parameter.

22 Claims, 31 Drawing Sheets

(56) References Cited

U.S. PATENT DOCUMENTS

| | | | |
|---|---|---|---|
| 5,591,130 A * | 1/1997 | Denton | 604/100.02 |
| 5,913,685 A * | 6/1999 | Hutchins | 434/265 |
| 6,236,989 B1 | 5/2001 | Mandyam et al. | |
| 6,262,730 B1 | 7/2001 | Horvitz et al. | |
| 6,398,727 B1 * | 6/2002 | Bui et al. | 600/300 |
| 6,477,531 B1 | 11/2002 | Sullivan et al. | |
| 6,799,205 B2 | 9/2004 | Ludtke | |
| 6,993,720 B1 | 1/2006 | Hanoch et al. | |
| 7,031,954 B1 | 4/2006 | Kirsch | |
| 2004/0054261 A1 * | 3/2004 | Kamataki et al. | 600/300 |
| 2004/0099263 A1 * | 5/2004 | Melker et al. | 128/200.26 |
| 2004/0152952 A1 * | 8/2004 | Gotlib et al. | 600/300 |
| 2004/0214148 A1 * | 10/2004 | Salvino et al. | 434/262 |
| 2005/0177096 A1 * | 8/2005 | Bollish et al. | 604/65 |
| 2005/0240441 A1 * | 10/2005 | Suzuki et al. | 705/2 |
| 2005/0249263 A1 * | 11/2005 | Yerlikaya et al. | 374/209 |
| 2007/0113849 A1 * | 5/2007 | Matthews et al. | 128/204.22 |
| 2008/0039735 A1 * | 2/2008 | Hickerson | 600/532 |
| 2008/0214906 A1 * | 9/2008 | Wang et al. | 600/301 |
| 2008/0251070 A1 * | 10/2008 | Pinskiy et al. | 128/202.22 |
| 2009/0031020 A1 * | 1/2009 | Garcia et al. | 709/224 |
| 2009/0099867 A1 * | 4/2009 | Newman | 705/2 |
| 2009/0099876 A1 * | 4/2009 | Whitman | 705/3 |
| 2012/0319816 A1 * | 12/2012 | Al-Ali | 340/5.8 |

OTHER PUBLICATIONS

Hekker, J. J in Computer Animated Graphics as a "Teaching Tool for the Anesthesia Machine Simulator", EUT Report 89-E-228, Oct. 1989, p. 1-67.*

NPL_intubation_videos_.pdf p. 1-4.*

* cited by examiner

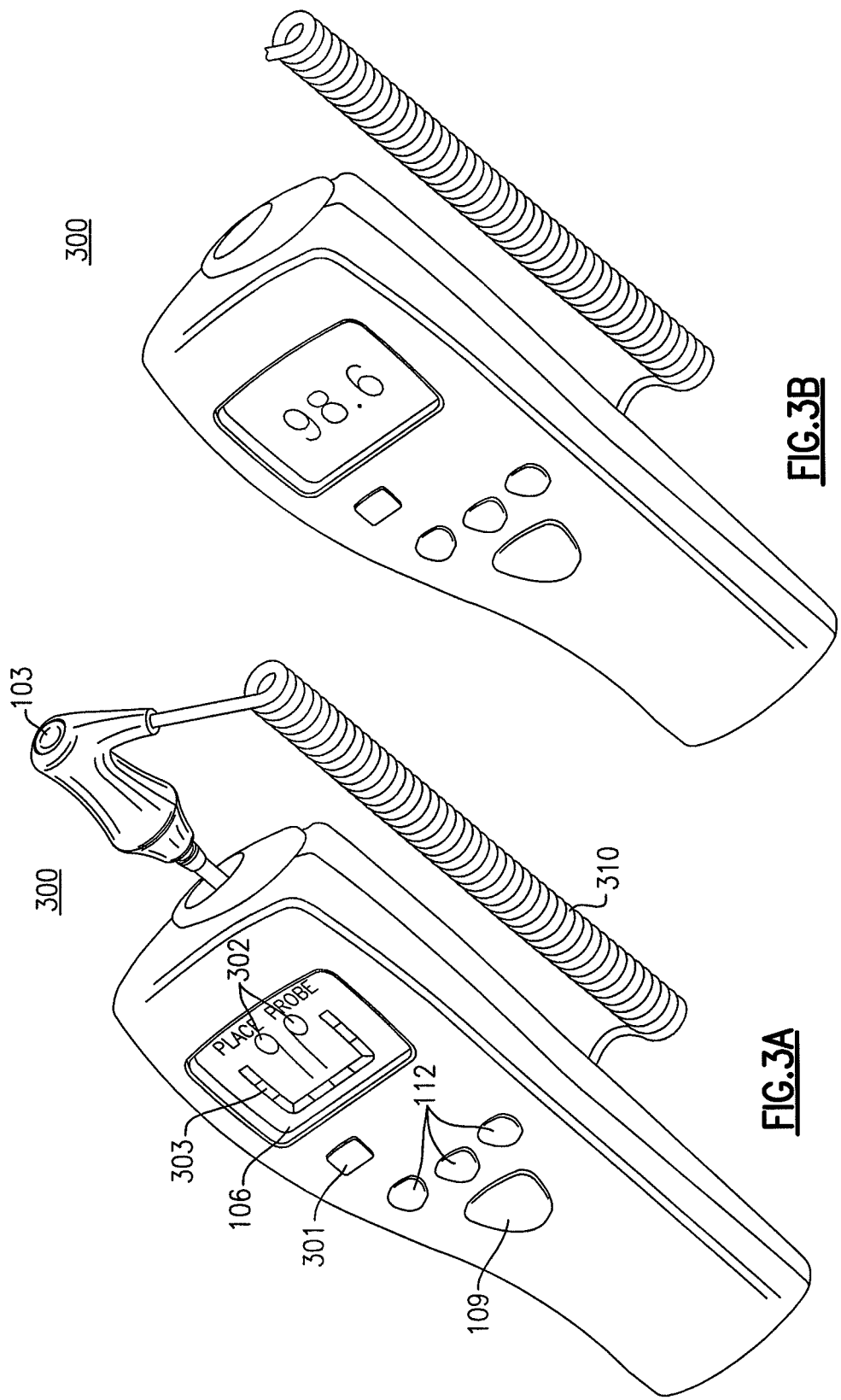

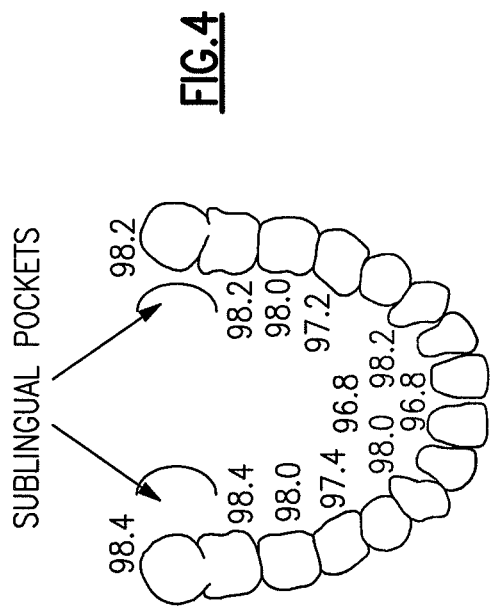

ON DEMAND HELP/IN-SERVICE FOR A MEDICAL DEVICE

FIELD OF THE INVENTION

The invention relates to medical equipment in general and more particularly to medical equipment that can automatically detect an operator error and provide assistance to the operator.

BACKGROUND OF THE INVENTION

Erroneous measurements from medical equipment can often be attributed to clinician operator error. A number of these errors relate to the clinician's lack of understanding of how to properly use the equipment or how to properly place physiological sensors. While these problems exist at all clinician skill levels, medical equipment operator errors are especially problematic in triage situations, ambulatory care settings, such as where a clinician periodically takes vital signs, and at company and school medical clinics.

At the lowest skill levels, when clinicians were asked how they use basic medical instruments, such as digital thermometers, clinical workers commented that the devices have too many features, modes, or settings that they do not know how to use. One clinician observed by analogy that a TV has lots of nice features, but the only buttons I know how to use are power, on/off, channel, and volume. Higher skilled clinicians, including registered nurses, have problems operating some medical equipment, simply because there are so many models and types that it is too difficult to become familiar and skilled with the features and operation of each one. Another problem is that higher skilled clinicians are less likely to ask for help. Either their peers or superiors are too busy for equipment operation questions, or some skilled clinicians are too embarrassed to ask for help and/or hesitant to show their lack of knowledge to others.

Some clinicians will do "whatever it takes" to make seemingly uncooperative medical instruments produce a reading that can be recorded. For example, clinicians using a feature rich digital thermometer were observed shaking and rattling the thermometer until it appeared to function. Even when the thermometer ended up in an incorrect mode, some clinicians still used the reading, not realizing that the reading was in error. In other cases, when the thermometer did not seem to give a useful reading, clinician's were observed to excessively move the temperature sensor around in the patient's mouth or to remove and replace it in the patient's mouth an excessive number of times.

While most medical equipment comes with an operating manual, such manuals are rarely easily accessible by the operator of the equipment. Generally the manuals end up in a difficult to access filing cabinet or worse yet, in the trash. Even in cases where medical equipment manuals are available to the operating clinicians, there is often little or no time for a clinician to read each manual.

There is a need for medical equipment that can assist a clinician in the proper use of the medical equipment during routine use. There is also a need for medical equipment that can automatically detect incorrect use and suggest a proper operation to the equipment operator.

SUMMARY OF THE INVENTION

In one aspect, the invention relates to a medical monitor including a physiological sensor. The physiological sensor is configured to measure a physiological parameter. The medical monitor also includes an electronic circuit configured to receive a signal from the physiological sensor. The electronic circuit further includes a microcomputer configured to process the signal from the physiological sensor and to generate a value representative of the physiological parameter. The microcomputer is also configured to cause the medical monitor to display an in-service help screen on a display on the medical monitor in response to a detection of a predetermined number of out of range values of the physiological parameter.

In one embodiment, the microcomputer is programmed with one or more instructions including an algorithm configured to determine whether the value representative of the physiological parameter is a value within a range of expected values.

In another embodiment, the microcomputer is programmed with one or more instructions including an algorithm configured to determine whether the value representative of the physiological parameter is a value outside a range of expected values.

In yet another embodiment, the medical monitor includes an oral temperature probe and the in-service help screen displays an image of a sublingual pocket.

In yet another embodiment, the medical monitor includes a temperature probe type selected from the group of probe types consisting of an oral probe, an axillary probe, and a rectal probe, and the detection of a predetermined number of out of range values includes detection of a predetermined number of out of range values expected for a particular selected probe type.

In yet another embodiment, the in-service help screen on a display includes a warning that an improper probe type mode may have been selected on the medical monitor.

In yet another embodiment, the medical monitor includes a respiration monitor based on an ECG measurement and the detection of a predetermined number of out of range values includes a detection of anomalous respiration.

In yet another embodiment, the in-service help screen on a display includes a warning that indicates insufficient or anomalous respiration and a suggestion to check ECG lead placement and ECG lead types In yet another embodiment, the medical monitor includes a SPO2 monitor and the detection of a predetermined number of out of range values includes a detection of anomalous SPO2 electrical levels.

In yet another embodiment, the in-service help screen on a display includes a warning that a defective SPO2 probe is suspected and a suggestion to replace the defective SPO2 probe.

In yet another embodiment, the medical monitor includes a CO2 monitor and the detection of a predetermined number of out of range values includes a detection of abnormally low CO2 levels.

In yet another embodiment, the in-service help screen on a display includes a warning that an esophageal intubation is suspected and displays an image showing an esophageal intubation.

In yet another embodiment, the medical monitor includes a capnography monitor and the detection of a predetermined number of out of range values includes a detection of an alveolar plateau that is rounded or "blunted" where it blends with the down stroke of the capnogram.

In yet another embodiment, the in-service help screen on a display includes a warning that an air leak is suspected and displays at least a selected one of: an image of a endotracheal tube cuff an image of a tracheal tube cuff, an image of an artificial airway showing a problematic airflow possibly due to an insufficient opening.

In yet another embodiment, the medical monitor includes a capnography monitor and the detection of a predetermined number of out of range values includes a detection of a slope of the ascending limb of the capnogram that has little or no alveolar plateau.

In yet another embodiment, the in-service help screen on a display includes a warning including at least a selected one of: warning that an endotracheal tube kink is suspected, warning that the patient airway is otherwise obstructed, warning that a recommendation for immediate intervention.

In yet another embodiment, the in-service help screen further includes suggestions of possible causes including at least a selected one of: suggestion if no visible kinks, consider bronchospasm, suggestion of COPD, suggestion of foreign body in the upper airway, suggestion of herniated endotracheal or tracheal tube cuff.

In yet another embodiment, the medical monitor includes a capnography monitor and the detection of a predetermined number of out of range values includes a detection of increasing EtCO2 values, and a capnography shows an elevated baseline or the capnograph waveform does not return to zero at the end of inspiration.

In yet another embodiment, the in-service help screen on a display includes a warning that Co2 re-breathing is suspected and a suggestion that an operator look for at least a selected one of: suggestion of an inadequate expiratory time, suggestion of a malfunctioning inspiratory valve, suggestion of an insufficient inspiratory flow rate, suggestion of a malfunction in the breathing circuit.

In yet another embodiment, the medical monitor includes a temperature probe and the detection of a predetermined number of out of range values includes a detection of a temperature measurement beyond a pre-determined temperature and the in-service help screen displays an instruction to an operator to order at least one pre-determined type of lab work based on the temperature measurement.

In yet another embodiment, a second parameter includes a measurement of time from an indicator of commencing a medical measurement to receiving a predetermined number of output values representative of the physiological sensor, and wherein on detecting a condition where the predetermined number of output values representative of the physiological sensor are outside of an expected range, the medical monitor is configured to display an intervention screen on a display on the medical monitor.

In yet another embodiment, the indicator of commencing a medical measurement includes removing the physiological sensor from a stored position.

In yet another embodiment, the indicator of commencing a medical measurement includes removing a temperature probe from a temperature probe storage well.

In one aspect, the invention relates to a medical monitor including a physiological sensor, the physiological sensor configured to measure a physiological parameter. The medical monitor also includes an electronic circuit configured to receive a signal from the physiological sensor. The electronic circuit further including a microcomputer configured to process the signal from the physiological sensor and to generate a value representative of the physiological parameter. The microcomputer is configured to process a second signal from a second sensor representative of a second parameter. The microcomputer is also configured to cause the medical monitor to display an in-service help screen on a display on the medical monitor in response to a detection of a predetermined number of out of range values of the second parameter.

In one embodiment, the microcomputer is programmed with one or more instructions including an algorithm configured to determine whether the value representative of the second parameter is a value within a range of expected values.

In another embodiment, the microcomputer is programmed with one or more instructions including an algorithm configured to determine whether the value representative of the second parameter is a value outside a range of expected values.

In yet another embodiment, the second parameter includes a signal from one or more accelerometers and the physiological parameter is a temperature parameter.

In yet another embodiment, the second parameter includes a signal from a biting sensor and the physiological parameter is a temperature parameter.

In yet another embodiment, the second parameter includes a signal from an ambient light sensor and the physiological parameter is a SPO2 parameter.

In yet another embodiment, the second parameter includes a NIBP measurement and the physiological parameter is a SPO2 parameter and wherein a comparison of the NIBP measurement with the SPO2 parameter tests for distortion of an SPO2 caused by operation of an NIBP cuff.

In yet another embodiment, the second parameter includes a temperature measurement to determine proper contact of a NIBP cuff with a person's limb.

In yet another embodiment, the second parameter includes a measurement of time from an indicator of commencing a medical measurement to receiving a predetermined number of output values representative of the physiological sensor, and wherein on detecting a condition where the predetermined number of output values representative of the physiological sensor are outside of an expected range, the medical monitor is configured to display an intervention screen on a display on the medical monitor.

In yet another embodiment, the second parameter includes an indication of a maintenance problem.

In yet another embodiment, the indication of a maintenance problem includes an out of paper indication.

In yet another embodiment, the in-service help screen on a display on the medical monitor includes one of selected in-service help screens, at least one instructional video and at least one instructional image, both demonstrating how to change the paper.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 3A shows a drawing of an exemplary embodiment of a thermometer showing a recommended probe placement according to the invention.

FIG. 3B shows the thermometer of FIG. 3A displaying a measured temperature.

FIG. 4 shows an exemplary drawing of the mouth showing proper placement of a thermometer probe in the sublingual pocket.

FIG. 5 shows a chart of normal body temperature ranges for oral, rectal, axillary, ear, and core temperature measurement methods.

DETAILED DESCRIPTION OF THE INVENTION

Figure 1A:
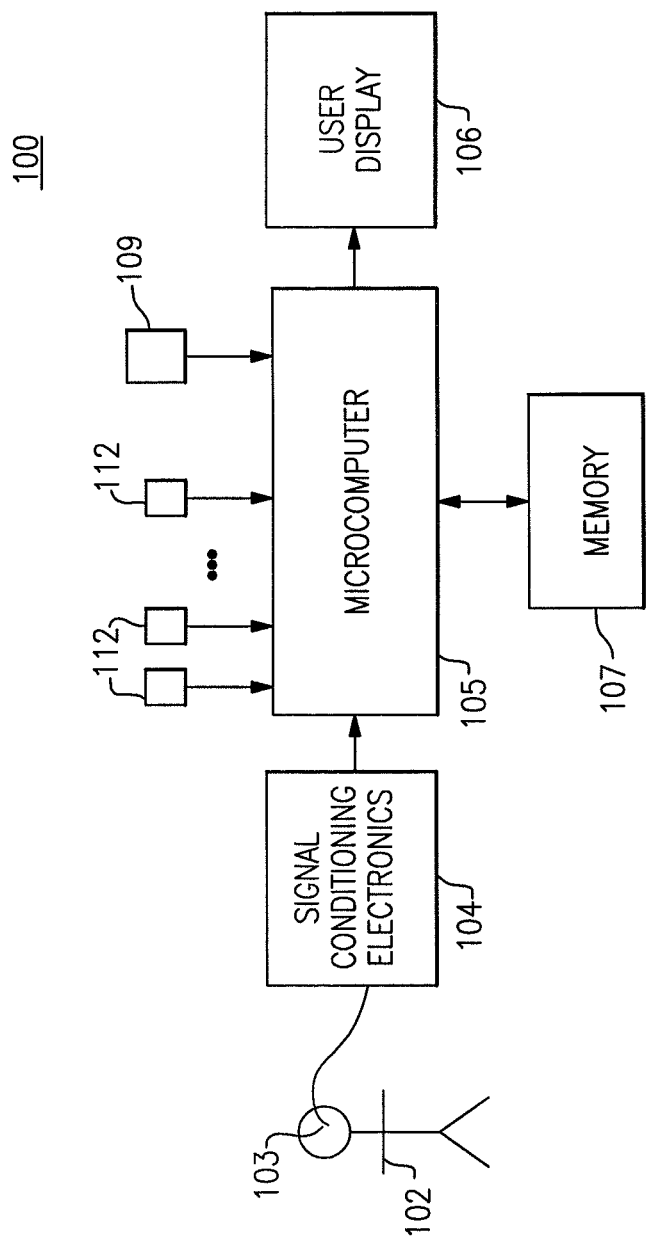
FIG. 1A shows a block diagram of an exemplary medical instrument according to the invention.

We describe a system and method for reducing erroneous measurements from a medical instrument, such as a medical monitor (referred to herein interchangeably as "medical equipment" or "medical instrument"), that can be attributed to clinician operator error. Since these errors generally relate to the clinician's lack of understanding of how to properly use the equipment or how to properly place physiological sensors, our hierarchical system and method can provide in-service "on-demand" help tailored to a specific clinician operator need. The hierarchical system and method is a heuristic approach beyond a conventional "help" menu system of the prior art, which simply provides a contents or index of available help pages. Our "in-service" or "on-demand" help system and method can be roughly organized into three types of in-service clinician operator assistance. According to one type of in-service or on-demand help, a clinician realizes that they need further assistance and queries the medical equipment for help. According to another type of in-service or on-demand help, some feature of the medical equipment is accessed and at least one clinician action has occurred, such as removing a probe from a probe holder or well, yet within a certain pre-determined time, a successful measurement has not yet been made, causing the medical equipment to generate on offer of assistance. According to yet another type of in-service or on-demand help, the medical equipment can detect a pending clinician operator error by analyzing data from a physiological sensor or an additional sensor for monitoring the execution of a given measurement type and for assessing the validity of the desired physiological measurement. The medical equipment can intervene by offering assistance in the form of in-service help to the clinician operator.

Medical equipment employing our inventive in-service or on-demand help system and method can use any one of the three types of in-service or on-demand help, the three types of in-service or on-demand help in any combination, or a hierarchical system of any of the three types of in-service or on-demand help. In the description which follows, we explain the three types of in-service or on-demand help in more detail. In general, "on-demand" help features are requested by an operator of the medical equipment, while "in-service" help can be "offered" to the operator of the medical equipment where the offer is originated by the medical equipment itself.

Operator Requested Assistance:

In medical equipment of the prior art, generally pressing a "help" button takes an operator to a generic menu tree offering navigation through a table of contents or an index of all medical help text pages available or pre-programmed into a specific medical equipment box. At best, a proffered text menu might have some relevance to a selected equipment mode, such as relevant to a selected type of measurement. Our research with the clinical community suggests that such generic table of contents or index based help is ineffectual and can waste time in critical care situations.

In the various embodiments of our operator requested assistance approach, also functional as a first level in a hierarchical system and method, the medical equipment offers far more target specific and directed help in response to an operator request for help. In other words, in one embodiment, using heuristics built into the software operating on a microcomputer in the equipment, an algorithm can consider a plurality of input factors when tailoring a response to a user who presses the help button.

Assistance Provided when a Measurement Takes Too Long:

In another embodiment of medical equipment, assistance can be offered and provided by the medical equipment, where it takes an operator too long to accomplish an operator task. For example, the medical equipment can time how long it takes from commencing a measurement to a first valid measurement. Where the medical equipment determines that an operator task is taking too long, the medical equipment can offer help, such as in a displayed message offer of assistance. A help scheme based on elapsed time can be a stand alone in-service help mode. In other embodiments of medical equipment having a hierarchical system and method for "in-service" and "on demand" help, help based on time elapsed can be provided, for example, as a second level of assistance.

Example 1

Figure 8:
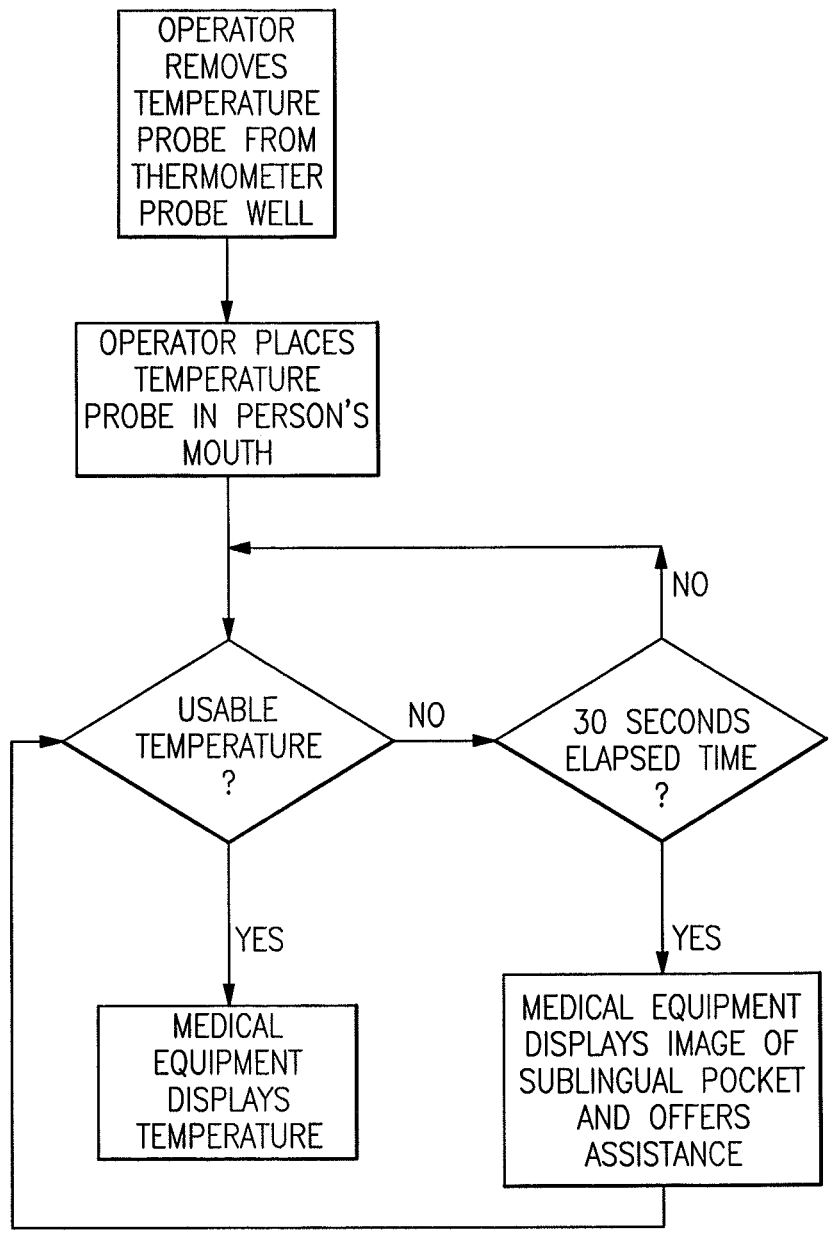
FIG. 8 shows a flow chart illustrating a thermometer offering in-service help based on a time interval.

Medical equipment including a thermometer probe supplied in a thermometer probe well incorporates a timed task help scheme as illustrated by the flow chart of FIG. 8. The equipment is set to a temperature measurement mode suitable for making an oral temperature measurement. The operator removes the temperature probe from the thermometer probe well. The operator then incorrectly places the temperature probe in a person's mouth, far from the proper placement in a sublingual pocket of the mouth. The medical equipment reaches a pre-programed time of 30 seconds without achieving a usable temperature measurement. The temperature measurements are varying too much in time to present a valid measurement and/or are too low to represent a valid oral temperature measurement. The medical equipment presents an offer of assistance. An exemplary help display can show an image of an oral thermometer probe correctly placed in a sublingual pocket. The image can flash one or more times to draw attention to a display screen and/or text can flash asking if further assistance is desired. The assistance display can also offer the operator a convenient way to cancel the assistance display.

In this elapsed time help scheme, as well in other user demanded, or equipment provided help displays, the underlying measurement, even where suspected to be in error, can still be visibly displayed where possible. For example, in this example, a temperature measurement that is thought to be too low, or a fluctuating temperature can be displayed as visible numbers either slightly "grayed out" under the assistance screen, or in another window within or adjacent to the displayed assistance screen.

An elapsed time based in-service help scheme can be useful for detecting potential operator errors beyond those identified by the time it takes to complete a given task. For example, there can be certain types of measurements that need operator actions after a certain period of time, even where the probes and sensors have been properly placed by the operator.

Example 2

Figure 9:
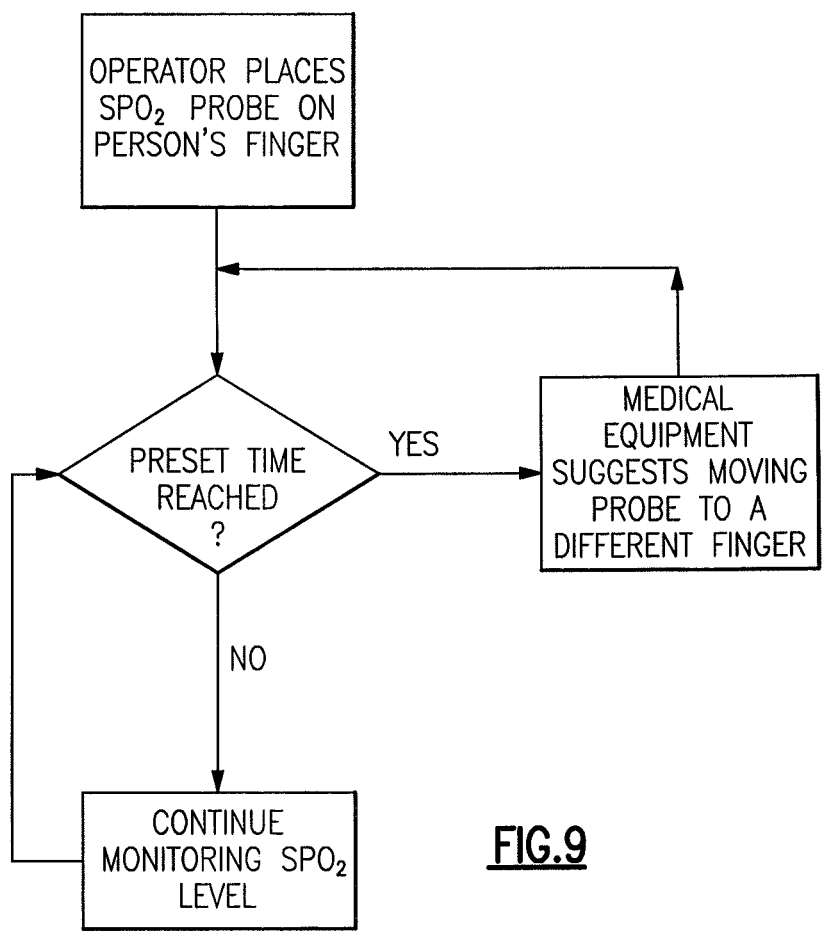
FIG. 9 shows a flow chart illustrating a $SPO_2$ monitor function offering in-service help based on a time interval.

An $SPO_2$ probe, pulse oximetry probe has been properly placed on a person's finger and is producing valid usable $SPO_2$ measurements. However, if the probe is left in place on the person's finger in the same position for a long period of time, there can be skin burn, or some breakdown of the skin. The medical equipment monitor, as illustrated in the flow chart of FIG. 9, can begin a long term timer when the $SpO_2$ probe is first placed. After a pre-set period of time, the monitor displays an assistance message noting the time the $SpO_2$ probe has been in place and suggesting movement of the $SpO_2$ probe to another finger to avoid skin damage.

An elapsed time based in-service help scheme can also be useful for detecting potential operator errors related to medical equipment alarms. When medical equipment alarms sound too often or for conditions not requiring immediate attention in a given situation the alarms can become a nuisance. Another problem related to "false" alarms is that more critical alarms might be overlooked or ignored. When a medical instrument consistently presents alarms beyond a predetermined elapsed time for that situation, the medical equipment can offer assistance displays having recommendations on how to reduce the time and/or rate of alarms. For example, where a heart rate (HR) alarm is occurring 40% of the time in comparison to other alarms, a display screen can suggest that after checking the patient, different alarm limits might be more appropriate for the given patient's situation. A button with a software generated label, or a "pop up" menu option can appear to ask the operator if they would like further assistance in setting alarm levels. More sophisticated medical equipment can also make recommendations for more optimal alarm settings based on a recent alarming trend, while warning of possible consequences of overlooking patient conditions or conditions that could be missed at the higher alarm settings.

Equipment Intervention Based on Measured Parameters:

Preferably an operator measurement error can be detected and corrected before erroneous medical measurements make their way into medical diagnostic use. Another solution for reducing the number of clinician operator errors is to configure medical equipment to detect operator errors and to positively intervene with concise directions to correct an operator error. Detection and intervention can be a stand alone in-service help system or can be incorporated into medical equipment as another level in a hierarchical system and method of "on demand" and "in-service" help. To accomplish a medical equipment intervention, the medical equipment can include measurement data analysis and/or additional hardware sensors to detect a measurement error as it is occurring and preferably before erroneous readings are recorded or relayed for medical use.

Some existing medical equipment can display errors. The operator is left to try to interpret an error number and/or brief error text label. One aspect of the instant invention that distinguishes over conventional medical equipment error detection and error messages is that the medical equipment according to the inventive method and system displays one or more complete solutions to eliminate the error, rather than simply announcing an error and leaving the operator to search for solutions. Moreover, in some embodiments of the inventive system and method, emphasis can be placed on displaying information in image or moving image forms. Since studies have shown that typical medical equipment operators are more responsive to information presented in image form, it can be expected that more errors can be quickly mitigated by the operator using a more positive intervention solution driven intervention than mere conventional display of an "error".

In the intervention which follows from a detection of an operator error, the medical equipment can positively assist the operator to discontinue an erroneous measurement, pause for an instructional interaction with the medical instrument, and then to proceed with a corrected measurement technique towards a valid measurement. In the various embodiments and examples, we use a variety of techniques to detect an operator error as it occurs. In general, detection can be made by a real time analysis of measurement parameters. The measurement parameters can include the actual physiological parameter being measured and/or a secondary parameter being monitored solely for the purposes of measurement error detection. In the case of monitoring the physiological parameter being measured, software can monitor the parameter to determine if it falls within expected limits as well as to monitor change of the parameter with time. In other embodiments, additional sensors, such as position sensors, can be employed to monitor operation of the medical equipment and/or its various probes and sensors. If a position sensor determines a position of a physiological probe inconsistent with proper measurement procedure for that instrument, an intervention can be made in the form of a positive offer of instructional assistance to the operator inadvertently about to make an erroneous measurement.

Many of the embodiments herein make use of an automatic detection of an operator measurement error followed by an intervention by the medical equipment. There can also be present an operator accessible path to the same medical equipment offered assistance. Such direct access can be via a "help" or "assistance needed" button. Such buttons can be hardware buttons. Hardware buttons can have labels on the button, nearby the button, or on a display as generated by software and displayed as labels in the vicinity of a hardware button. Alternatively, a "soft" button can appear on a touch sensitive screen or surface.

We also note that it is conceivable in unusual circumstances that a clinician operator might have developed an alternative valid operational technique unknown to the manufacturer of the medical equipment. In such cases, a clinician operator can be offered an opportunity to escape from an instrument detected operator error and suggested instructional intervention.

Once an operator error in progress has been detected, the method of intervention can be as important as the act of error detection. The intervention should be done in a way that remedial guidance can be quickly and succinctly communicated to a clinician operator. Such interventions can be a single step, or include several steps. The intervention, however, must be fast and directly responsive to the detected error, otherwise the operator will likely spend more effort escaping the intervention than heeding the proffered advice. One realization, largely based on observations by the inventors of clinical workers making medical measurements, is that clinicians appear to be more receptive to instruction based on a picture showing correct instrument operation or probe placement. Graphical information, including lines, arrows, and brief text can be added to enhance the guidance offered as a picture form, such as by image or video. Text based direction, while useful in some circumstances, such as an operator request for more information beyond an instrument proffered picture, has in general been observed to be less effective. In other embodiments, audio guidance, such as "text to voice" can be offered simultaneously with a picture (image or video). Such presentations, simultaneously using multiple human senses, can be more effective than text alone. While audio instruction can be helpful in some circumstances, in a busy critical care situation where several clinicians can be communicating at the same time and several measurements are being made by several equipment operators at the same time, audio directions might be less desirable. Where audio assistance is available and/or has been inadvertently selected, a clearly marked silence option can prevent further disorder in such situations.

We first describe several embodiments of the invention with respect to a variety of generic medical measurement and monitoring equipment. FIG. 1A shows a block diagram of an exemplary medical instrument 100 according to the invention. One or more sensors 103, can measure one or more physiological parameters of a person 102. A single exemplary temperature sensor 103 is shown in FIG. 1A. Sensor 103 can be coupled, generally by a direct electrical connection, to signal conditioning electronics 104. Signal conditioning electronics 104 typically includes one or more of the following electrical functions: filtering, over voltage or over current protection, amplification, and/or signal scaling including electrical gain or offsets. A microcomputer 105 can read an electrical value from sensor 103 and programmatically convert it to a corresponding physiological value, such as to degrees centigrade in the case of a temperature sensor. It is understood that digitization of an electrical value representative of a physiological sensor 103 can be accomplished by an analog to digital converter (ADC). It is unimportant whether the ADC is external to microcomputer 105 or included within microcomputer 105 as is understood in the exemplary block diagram of FIG. 1A. One or more buttons 112 can be used to select instrument modes and options. In some embodiments, a "measure" button 109 can be made more predominant than other buttons 112 by shape and/or color or otherwise made distinguishable from other user operated buttons 112 for ease of use. The physiological value can then be displayed on a user readable display 106, usually following operation of a measure button 109. In this exemplary embodiment, embedded medical equipment software running on microcomputer 105 can also compare measured physiological data to a stored data profile, such as can be stored in memory 107. Memory 107 can be any type of non-suitable non-volatile memory for storing pre-programmed data. A stored data profile can be as simple as a set of limits, such as a minimum and/or maximum value or be more complex, such as one or more expected profiles of data, such as expected profiles of ranges of data with time.

Figure 1B:
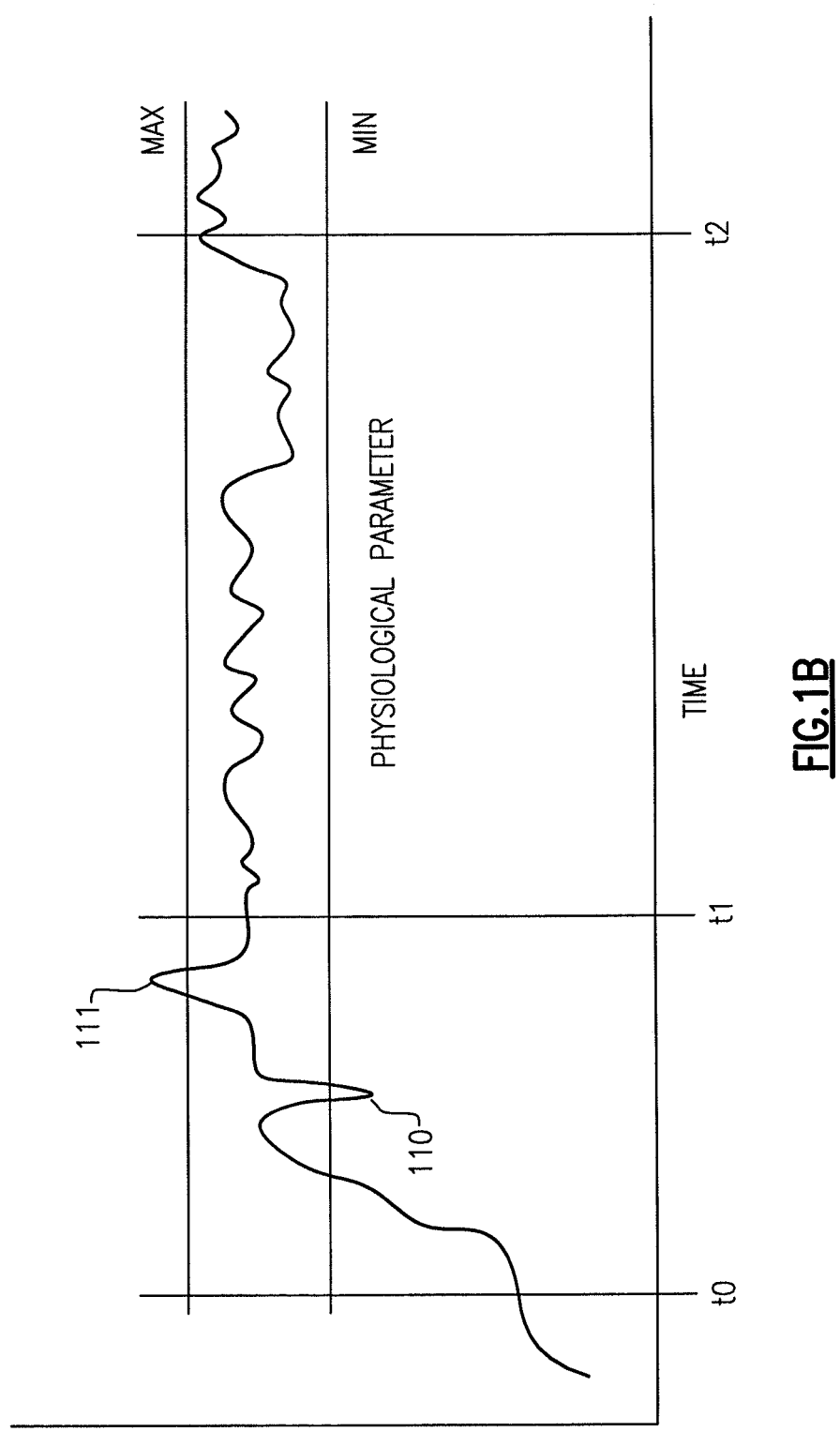
FIG. 1B shows a graph displaying a measurement of a physiological parameter with time.

FIG. 1B shows a graph of an exemplary measurement of a generic physiological parameter. In this embodiment of the invention, the program running on microcomputer 105 detects that a measurement is about to be made. Such detection can result from a button press, such as by pressing user operated measure button 109, or by automatic detection of changing input values, such as a rising parameter after time t0 as shown in the graph of FIG. 1B. Such a changing value can be typical of a changing parameter as caused by an initial placement of a physiological sensor 103 on a person 102. In one embodiment, the software can be programmed so as to allow an interval of time, shown as from t0 to t1, for the sensor to stabilize and properly report the intended physiological parameter being measured. The parameter of interest can then be generally expected to remain with some expected limits as shown by MAX and MIN following time t1. Such limits can be wide enough to allow for a normal expected range of readings. The software running on microcomputer 105 can be programmed to identify rapid changes 110 and 111 as appearing before t1. However, after a period of time, such as following time t1, the software can monitor the physiological value being measured as remaining within some expected profile with time. Variation from the expected profile, such as an out of limits reading or one or more rapid changes in the reading after time t1, but before completion and display of a reading at for example, a time t2, can suggest an operator error in using the medical equipment. The software can be programmed to respond to such erroneous reading by offering assistance to the user via the display 106. Where display 106 is a text only display, help can be offered in the form of textual explanation relevant to common known causes for present error. When a graphics display is present, such as a graphical LCD or other matrix type display, an operator can preferably be offered a picture or a brief movie tutorial on the proper operation of the equipment and/or the proper placement of the sensor 103, such as a physiological probe.

Figure 1C:
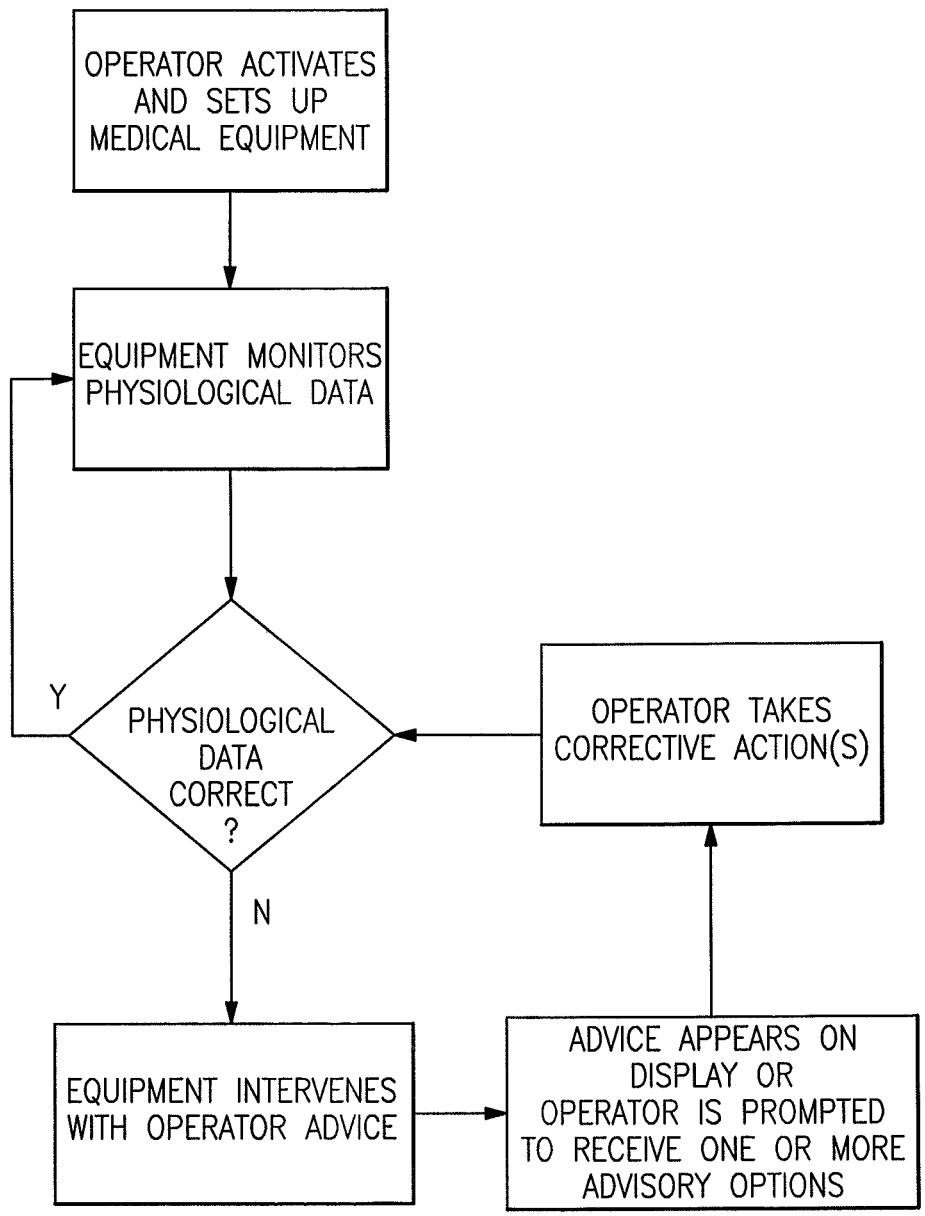
FIG. 1C shows a flow chart of the inventive method as illustrated by FIG. 1A and FIG. 1B.

FIG. 1C shows a flow chart of the inventive method as illustrated by FIG. 1A and FIG. 1B. In slightly more general terms, a medical equipment operator activates and sets up the medical equipment, including positioning or affixing any related electrodes, probes, or sensors. The medical equipment begins to receive and monitor physiological data from a person. Based on the incoming physiological data, for example data measurements acquired over time, or data compared to minimum and/or maximum limits, the medical equipment determines if the physiological data appears to be credible or correct for the operator intended measurement. The operator intended measurement can be inferred by the medical equipment, for example, by the types of sensors used, modes selected, and other medical instrument options selected by the operator or programmed into the medical equipment software by the manufacturer or configurations made for a specific clinical setting. If the incoming measured physiological data appears to be consistent with the desired measurement and/or mode selected by the operator, the medical equipment continues to monitor the measurements. If the data does not appear to be correct, the medical equipment can make a positive intervention to attempt to correct a probable operator error. The intervention can be, for example, in the form of a prompt for one or more types of assistance based on one or more problems attributed by the medical equipment as the determined or probably cause of the problem or problems. Or, the medical equipment can select a most likely cause and display without prior prompting or operator response, for example, a picture or image suggesting remedial action, such as a picture showing a proper probe placement or a picture of a section of the front panel of the equipment suggesting which buttons the operator should push, as in to enter a more suitable mode for a present sensor configuration. Following the positive intervention by the medical instrument, the operator can take corrective actions, preferably, but not necessarily, as recommended by the medical equipment. If the operator's corrective action is successful, the medical instrument can detect a successful intervention and corrective action by the operator by noting correct incoming data and return to a monitoring state. If the operator action is not successful, the medical equipment can again suggest the most likely cause and how to remedy the situation with an offer of advice, such as by prompting. Or, the medical equipment can automatically display the advice, as by displaying another advisory image. The medical equipment can further offer an operator an escape from advice and/or data monitoring (not shown in FIG. 1C).

Figure 2A:
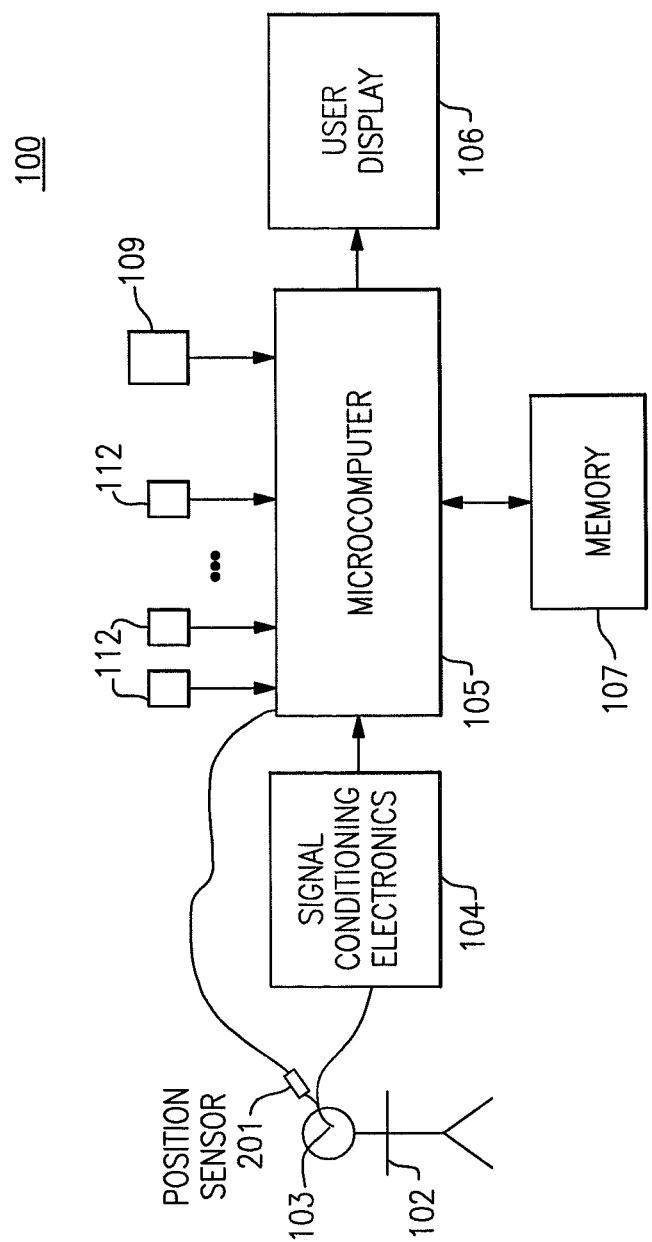
FIG. 2A shows a block diagram of an exemplary medical instrument using a position sensor.
Figure 2B:
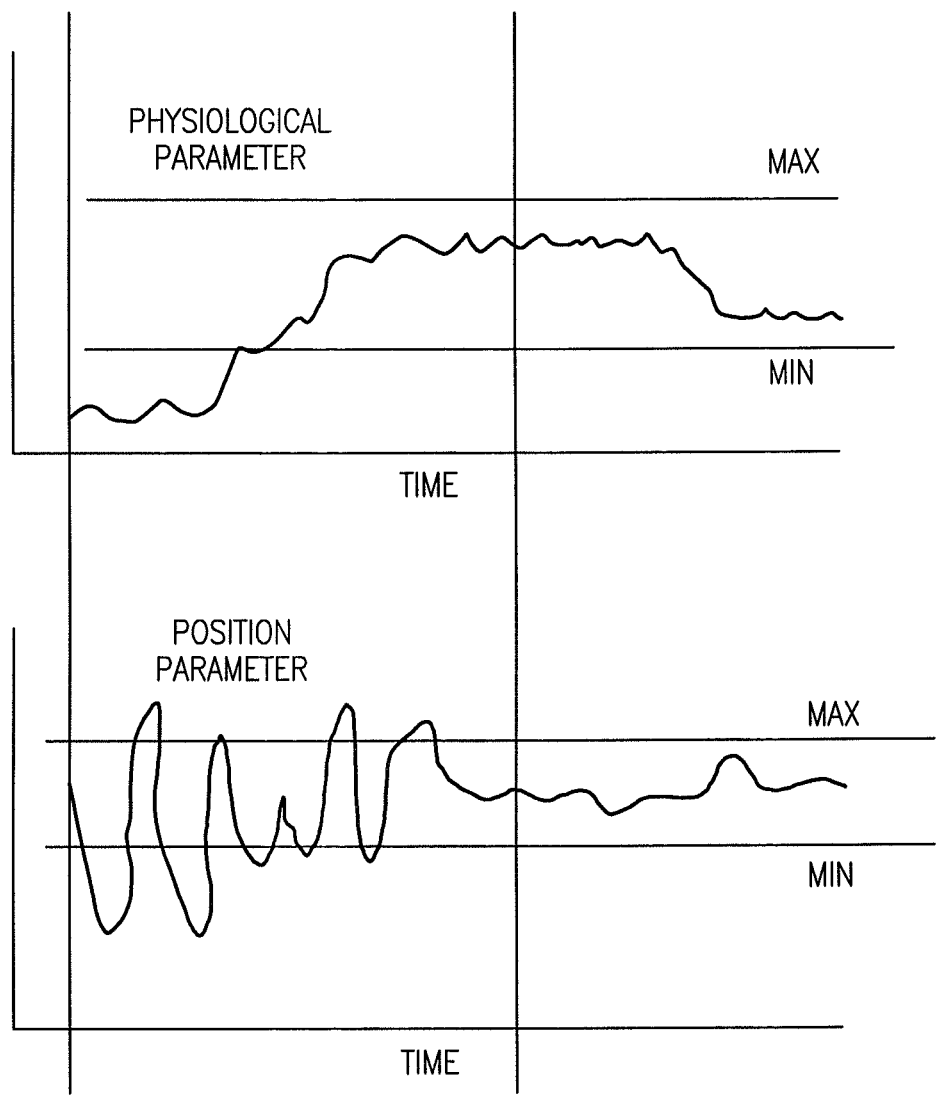
FIG. 2B shows a graph displaying a simultaneous measurement of a physiological parameter and probe position with time.
Figure 2C:
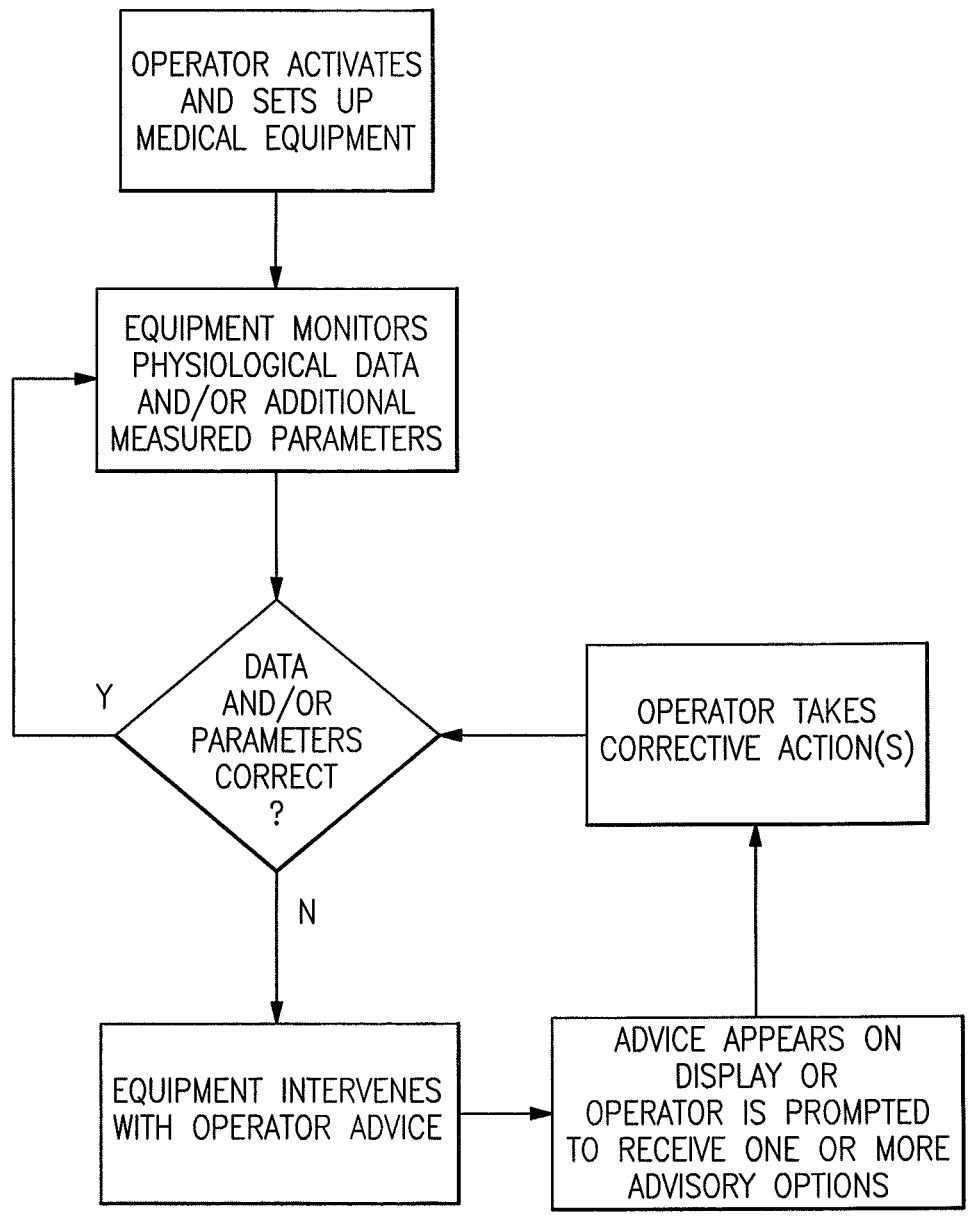
FIG. 2C shows a flow chart of the inventive method as illustrated by FIG. 2A and FIG. 2B.

In another embodiment of a medical instrument according to the invention as illustrated by the block diagram of FIG. 2A, one or more additional sensors 201 can be added to a medical instrument or medical probe or sensor to monitor one or more parameters in addition to the physiological parameter or parameters of interest. For example, sensor 201 can be a position sensor, such as a sensor that can detect a tilt angle of a portable instrument or of a sensor probe body, probe handle, or similar sensor fixture or housing. As shown by the graphs of FIG. 2B, the software running on a microcomputer 105 can be programmed to allow an interval of time, shown as before time t1, for the readings from one or more physiological sensors to stabilize, such as in waiting for a proper placement on the patient and where the one or more physiological sensors are properly reporting the intended physiological parameters being measured. After an interval of time, such as after a time t1, and/or detection and recognition of "good data" being measured, the software can consider if the readings from the one or more secondary sensors 201 are within limits. For example, in a case where the physiological data is seemingly valid, but where measured data from a sensor 201 suggests an incorrect probe or instrument orientation, display 106 can indicate there is a potential problem and offer assistance or automatically show a picture demonstrating a proper probe or sensor orientation. Such help can also be offered in text, pictures supplemented by text overlay, or video. Audio messages can also be used to supplement any text images, or video. Audio messages can be used where no text is present on the display and/or read any text on a display, or offer additional assistance beyond any visually displayed text, FIG. 2C shows a flow chart of the inventive method as illustrated by FIG. 2A and FIG. 2B. In slightly more general terms, a medical equipment operator activates and sets up the medical equipment, including positioning or affixing any related electrodes, probes, or sensors. The medical equipment begins to receive and monitor physiological data and/or one or more additional measured parameters from a person. Additional measured parameters can include, for example, orientation or position information regarding the positioning of a sensor or probe. Such orientation or position information can be obtained, for example, by use of accelerometers and/or gyros situated in or on a probe or sensor. Suitable accelerometers and/or gyros are available from a number of manufactures including accelerometers available from a number of companies including: Freescale Semiconductor of Austin, Tex., Analog Devices of Norwood, Mass., Infineon Technologies of Los Angeles, Calif., Memsic of Andover, Mass. and China, Bosch Sensortec of Reutlingen, Germany, Hitachi Metals of Tokyo, Japan, Oki Electric Industries of Tokyo, Japan, and Kionix of Ithaca, N.Y. Based on the incoming physiological data and/or one or more additional measured parameters, for example data measurements acquired over time, or data compared to minimum and/or maximum limits, the medical equipment determines if the physiological data and/or one or more additional measured parameters appears to be credible or correct for the operator intended measurement. The operator intended measurement can be inferred by the medical equipment, for example, by the types of sensors used, modes selected, and other medical instrument options selected by the operator or programmed into the medical equipment software by the manufacturer or configurations made for a specific clinical setting. If the incoming measured physiological data and/or one or more additional measured parameters appear to be consistent with the desired measurement and/or mode selected by the operator, the medical equipment continues to monitor the measurements. If the data or additional parameters do not appear to be correct, the medical equipment can make a positive intervention to attempt to correct a probable operator error. The intervention can be, for example, in the form of a prompt for one or more types of assistance based on one or more problems attributed by the medical equipment as the determined or probable cause of the problem or problems. Or, the medical equipment can select a most likely cause and display without prior prompting or operator response, for example, a picture or image suggesting remedial action, such as a picture showing a proper probe placement or a picture of a section of the front panel of the equipment suggesting which buttons the operator should push, as in to enter a more suitable mode for a present sensor configuration. Following the positive intervention by the medical instrument, the operator can take corrective actions, preferably, but not necessarily, as recommended by the medical equipment. If the operator's corrective action is successful, the medical instrument can detect a successful intervention and corrective action by the operator by noting correct incoming data and return to a monitoring state. If the operator action is not successful, the medical equipment can again suggest the most likely cause and how to remedy the situation with an offer of advice, such as by prompting. Or, the medical equipment can automatically display the advice, as by displaying another advisory image. The medical equipment can further offer an operator an escape from advice and/or data monitoring (not shown in FIG. 2C).

Thermometry Measurements:

Example 3

Figure 10:
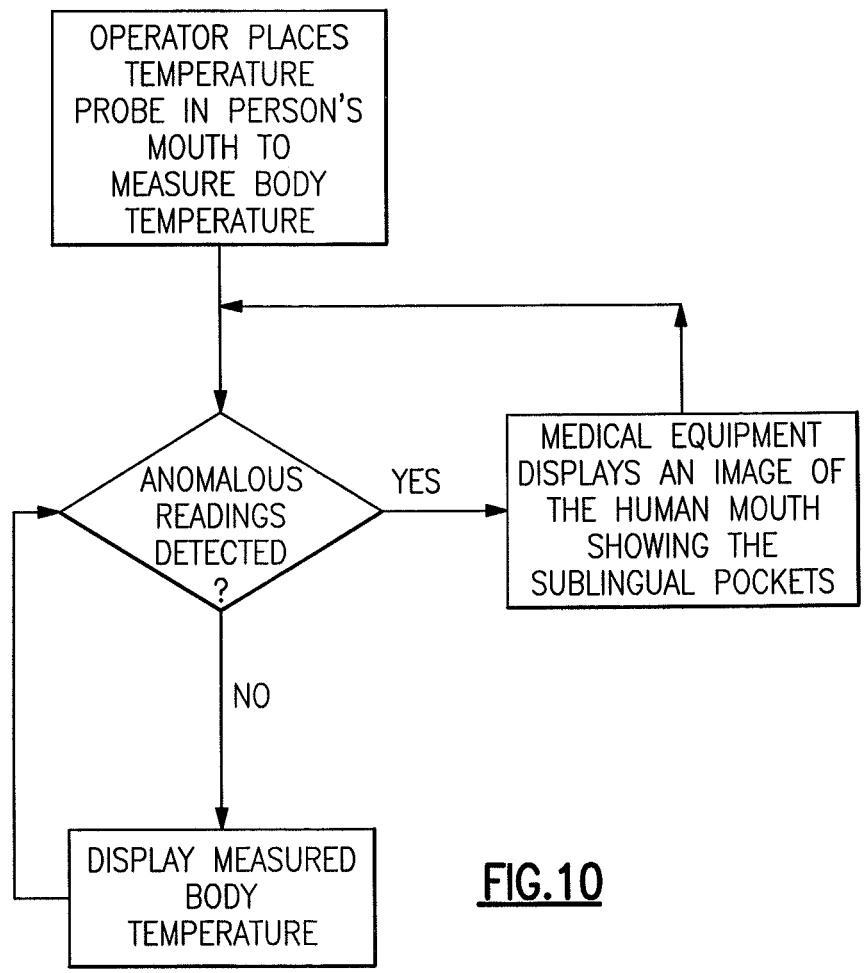
FIG. 10 shows a flow chart illustrating a thermometer offering in-service help based on an anomalous temperature measurement.
Figure 11:
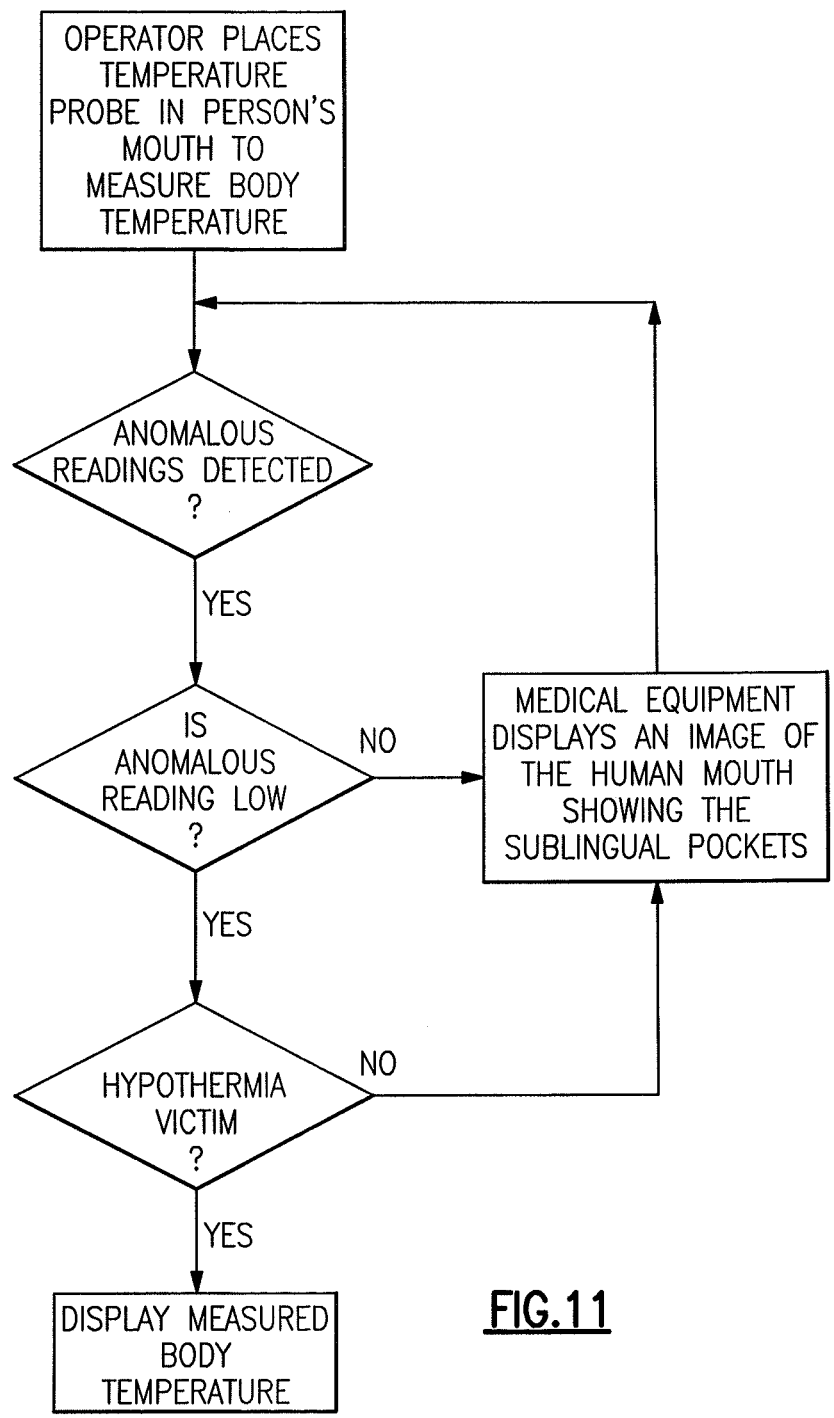
FIG. 11 shows a flow chart illustrating a thermometer offering in-service help based on an anomalous temperature measurement where the readings are low.

FIG. 3A shows one exemplary embodiment of a thermometer 300 as a medical instrument 100 configured according to the invention. In one embodiment, as further illustrated by the flowchart of FIG. 10, thermometer 300 can include a help button 301. Pressing help button 301 in the context of a temperature measurement can cause a view of a lower human mouth to be shown on display 106 in FIG. 3B. The exemplary image of a lower human mouth can show proper placement of a temperature sensor 103 in the sublingual pocket 302 of a mouth with respect to a lower row of teeth 303. Following a review of the image and correct placement of temperature probe 103 in a person's mouth, an operator can read a temperature measurement (FIG. 3B) by pressing measure button 109.

In another embodiment of the invention as shown in FIG. 3A, embedded microcomputer 105 (FIG. 1A) can be running software that analyzes temperature versus time. On detecting anomalous readings that suggest a clinician operator is having difficulty operating the instrument such as readings beyond the MIN or MAX limits of FIG. 1B, thermometer 300 can automatically offer a help image as shown in FIG. 3A, or automatically display the help image. A tutorial or in-service screen can be offered or displayed if the thermometer senses an improper curve or thermodynamic response as caused, for example, by poor tissue contact in the sublingual pocket.

In an embodiment of thermometer 300 having automatic operator error detection, a help button 301 may or may not be present. FIG. 3B shows a thermometer 300 displaying a measured temperature following proper placement of sensor 103. Sensor 103 can be attached to thermometer 300 by a flexible wire 310 or attached in a fixed position to thermometer 300 (not shown in FIG. 3A or FIG. 3B).

Example 4

Figure 3C:
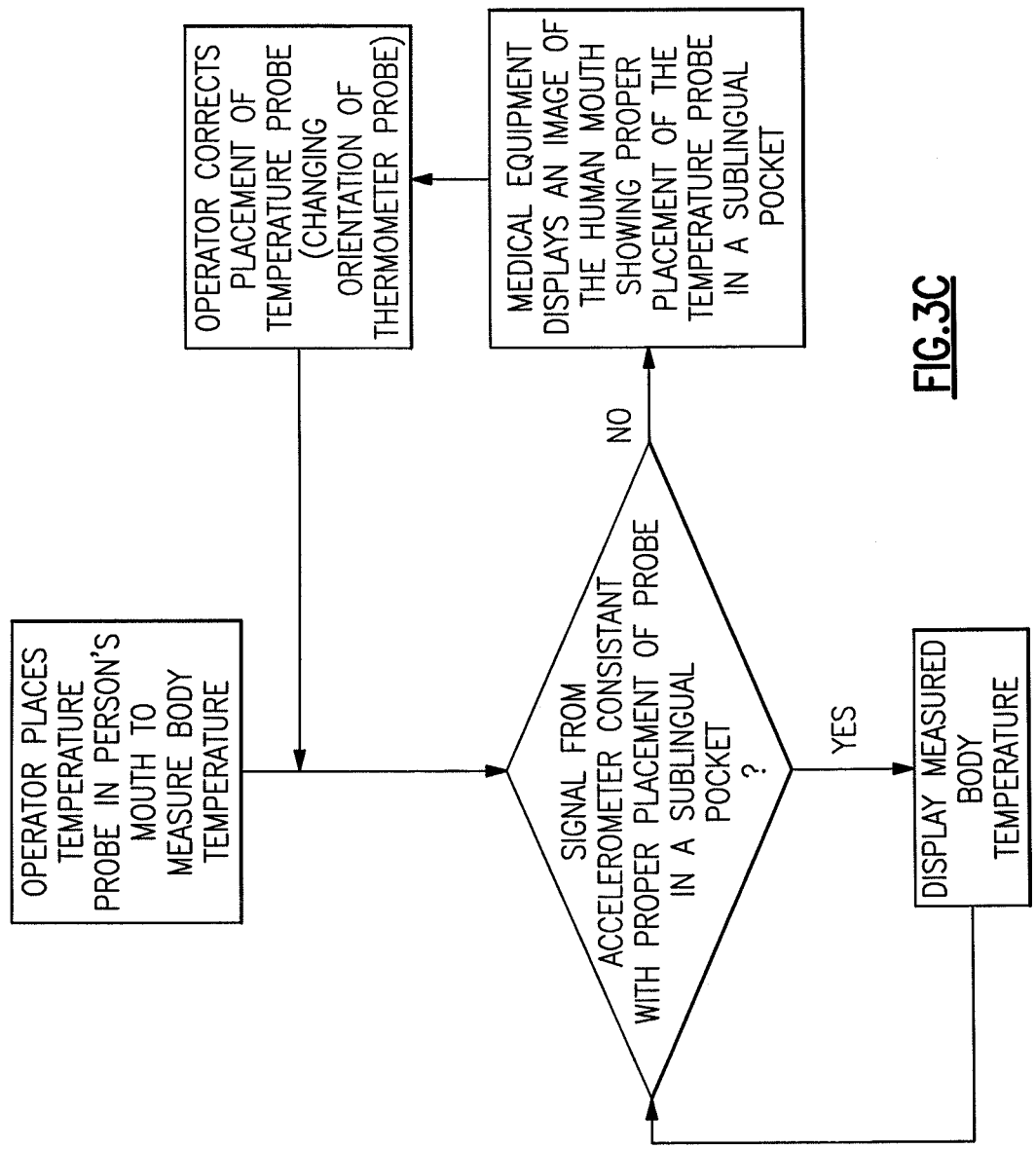
FIG. 3C shows a flow chart illustrating a thermometer offering in-service help based on an accelerometer signal.

The flow chart of FIG. 3C illustrates a system and method of in-service help for a thermometer 300 incorporating one or more accelerometers as additional sensors. An operator places a temperature probe into a person's mouth. The temperature probe has one or more accelerometers responsive to the position of the probe in addition to a temperature sensor. After a pre-determined period of time, an algorithm running on a microcomputer in the thermometer can evaluate the position of the probe based on the signal from the one or more accelerometers, such as for a person in a typical standing or sitting position. If the accelerometer information indicates a probe position inconsistent with proper placement of an oral temperature probe in a sublingual pocket, the thermometer can display an image of the sublingual pocket showing proper placement of an oral temperature probe. Following another period of time, the thermometer can re-evaluate the corrected placement of the probe based on new information from the one or more accelerometers. Where a probe physically separate from a monitor such as a dedicated temperature instrument or a medical monitor, the one or more accelerometers can be physically located in the probe. In the case of a compact "one-piece" thermometer, the one or more accelerometers can be situated anywhere in or on the body or the probe section of the thermometer.

In some very specific cases or in specialized embodiments, such as specific thermometer models as illustrated by the flowchart of FIG. 1, one or more questions can be posed to a clinical equipment operator before offering such help. For example, where an abnormally low temperature reading is detected (as represented by "MIN" in FIG. 1B), the software can be programmed to ask if person 102 is a hypothermia victim, before, or at the same time as, suggesting help with probe placement or equipment operation. In an exemplary case of a patient suffering from hypothermia such as after cold water drowning, the clinician can answer with an appropriate selection or other method of operator response, and proceed to make the desired measurement without further intervention by the instrument.

Example 5

Figure 12:
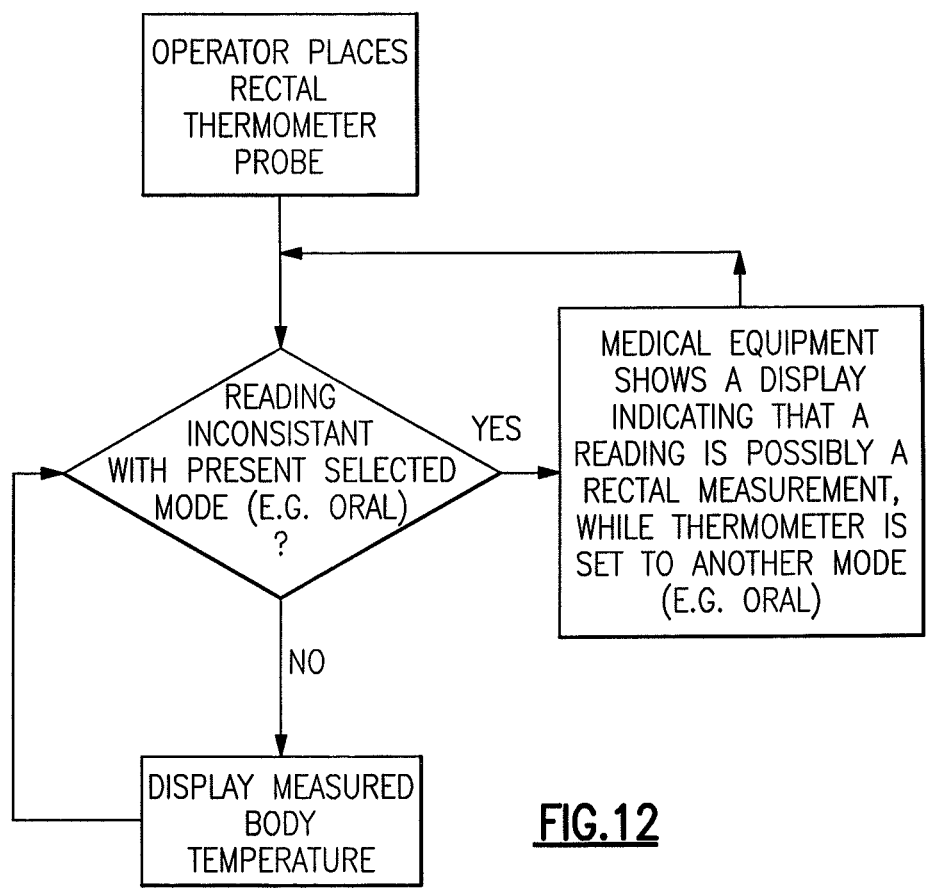
FIG. 12 shows a flow chart illustrating a thermometer offering in-service help based on an anomalous temperature measurement where the readings are inconsistent with the selected type of measurement probe.

A measured temperature value, or series of successive temperature readings, more consistent with a rectal reading, when a thermometer is in oral mode as shown in the flowchart of FIG. 12, can cause an in-service menu to pop up as the thermometer senses an abnormal response to the "mode" selected. It is understood in all examples herein, that there can also be present options for an operator of the medical equipment to "cancel out" of or to escape from any such error checking to avoid endless looping (an escape routine is not shown in FIG. 12 for simplicity).

In thermometry measurements in general, improper probe placement or incorrectly selected patient modes (neonatal to pediatric or adult for example) can be problematic. An advisory screen in text or image or combination of the two, can assist the clinician as to where they should place the probe (e.g. in the sublingual pocket, where a picture or drawing of the mouth can provide a helpful). FIG. 4 shows an exemplary drawing of the mouth showing proper placement of a thermometer probe in the sublingual pocket, similar images (not shown in FIG. 4) can indicate the proper placement of other types of probes.

Another indicator of possible operator error can be based on a normal range of temperatures expected for a given type of measurement taken from a standard body site used for thermometry. There are at least five standard temperature measurements based on different sites on the human body including, oral, rectal, axillary, ear, and core. FIG. 5 shows a chart of normal body temperature ranges for oral, rectal, axillary, ear, and core temperature measurement methods. As shown in FIG. 5, for a given actual body core temperature, the corresponding temperatures measure using one of the standard sites will vary, usually towards a lower value. Where the medical equipment, typically a thermometer, is set to make a temperature measurement, more sophisticated medical equipment typically has settings or modes that are set to correspond to the body site being used. Since the medical equipment, having been set to a particular mode for a given body site temperature measurement, expects a certain range of temperatures, and a certain range for "normal" temperature, that expectation can be used as an additional indicator of possible operator error leading to an intervention by the medical equipment.

Figure 6A:
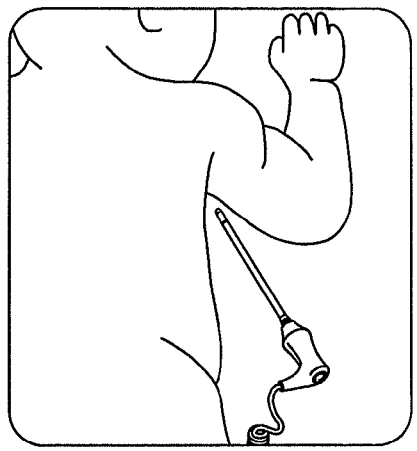
FIG. 6A illustrates a pediatric axillary temperature measurement.
Figure 6B:
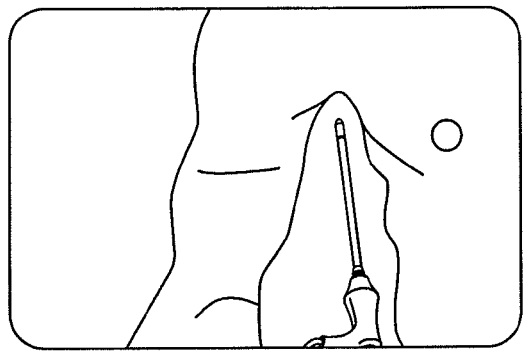
FIG. 6B illustrates an adult axillary temperature measurement.

An axillary temperature measurement can be made by placing a temperature sensing probe as high as practical into the under arm area (axilla) between the arm and the shoulder. FIG. 6A shows a pediatric axillary temperature measurement where the probe is placed high in the axilla and then the arm placed snugly at the child's side. FIG. 6B shows a similar measurement made on an adult person. Note that in both cases, a reading detected as low can result in medical equipment proffered help as a reminder to place the probe high in the axilla and to avoid folds in the skin.

Example 6

Figure 13:
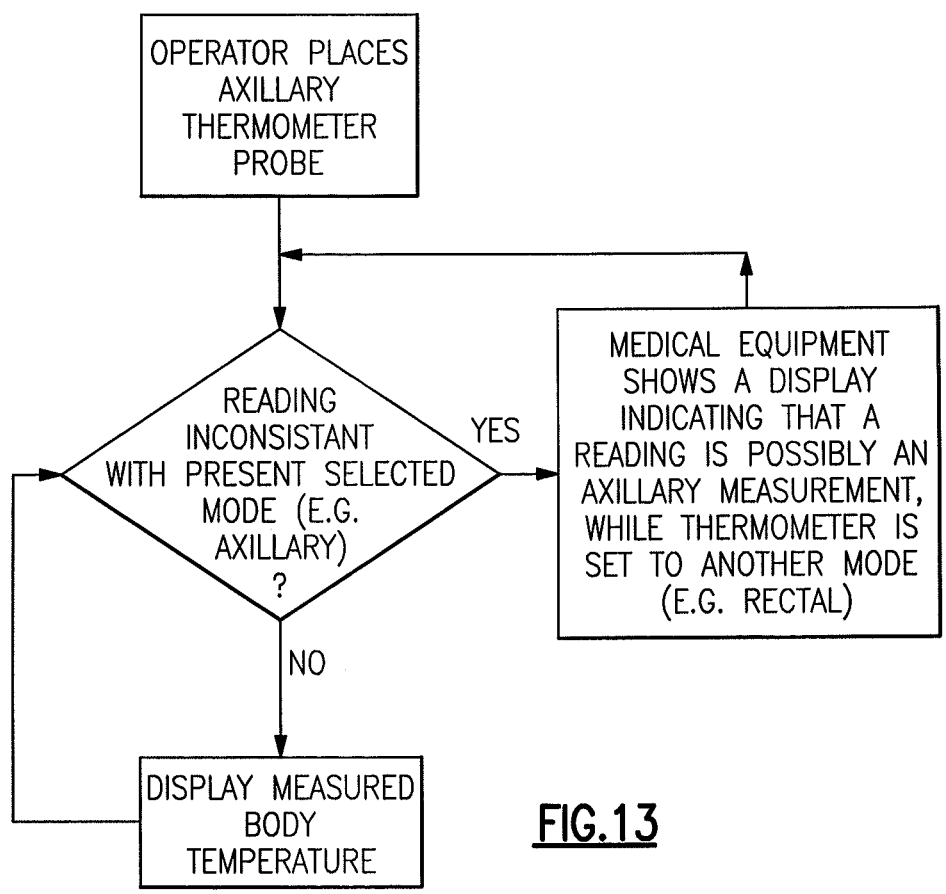
FIG. 13 shows a flow chart illustrating a thermometer offering in-service help where the readings are inconsistent with the selected axillary type of measurement probe.

A thermometer is set in a "rectal" mode. In many cases, there will be no correction or offset made to the measured temperature, however, the site where the measurement was made (i.e. the type of measurement) may generally be recorded, especially where a correction has not been made. Alternatively, the software running on a microcomputer in the thermometer can use calibration constants to convert the measured value from the thermometer probe to a corrected temperature for a given site, such as for a probe placed for a rectal measurement. Continuing with the example, the temperature readings, after some suitable time of stabilization, are registering at about 96.5° F. While not an impossible reading, there is a very high likelihood, as can be seen from the chart of FIG. 4, that an axillary measurement is actually being performed and that the instrument has been incorrectly set to the rectal mode through accidental key strokes or other operator error. An error detecting algorithm, also part of the software running on the thermometer's microcomputer, determines that the received values are more likely from an axillary measurement. A display on the thermometer displays the actual measurement, corrected for a rectal site, but flashes and also displays text prompting the operator to answer if the measurement is an axillary measurement. While offered a key to dismiss the warning or query, an operator answers by pressing a "yes" key, since it is actually an axillary measurement being made. In one embodiment of a thermometer according to this example and as illustrated by the flowchart of FIG. 13, following the "yes" answer, the thermometer reacts by automatically changing to an axillary mode, and displays the resulting corrected body temperature or uncorrected "raw" axillary temperature without flashing. In another embodiment, the thermometer calls attention to the display by such means as flashing, changing display colors, displaying warning text, optionally with some emphasis, such as a bold font, different font (e.g. size, style, color, underline, italics, etc.), or a flashing font. Again, the thermometer can ask the operator if an axillary measurement is being performed. If the answer is "yes", the thermometer display can offer a tutorial on how to change the thermometer from a rectal mode to an axillary mode. Such tutorials can be in the form of text, graphical display, pictures of the buttons to press, pictures of menu options, or movies showing how to change modes.

Figure 7:
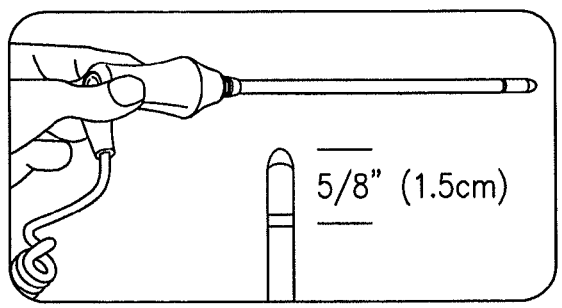
FIG. 7 shows an exemplary drawing of a rectal thermometry probe.

Another possible source of operator error in thermometry involves placement of a rectal thermometer probe. Optimal rectal temperature measurements generally call for a probe placement to a depth of about ⅝" or 1.5 cm as shown in FIG. 7. A more shallow insertion is likely to cause an erroneous low temperature reading. A deeper insertion can dramatically increase the risk of bowel perforation as well as providing a less accurate measurement result. A thermometer that can detect the amount of rectal insertion can react by intervening with helpful information. A thermometer set in a "rectal" mode has a rectal thermometer probe designed to indicate insertion depth using a second thermistor or some equivalent suitable type of depth sensor.

Example 7

Figure 14:
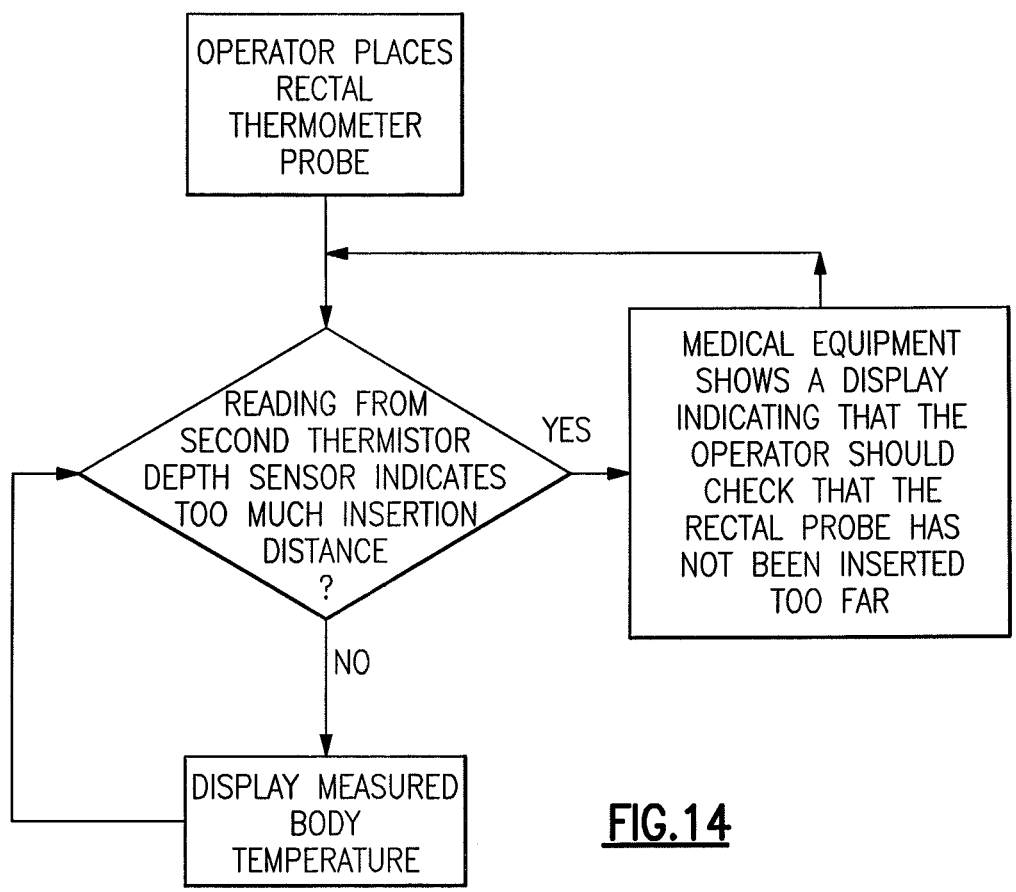
FIG. 14 shows a flow chart illustrating a thermometer offering in-service help where the readings from a second sensor are inconsistent with proper insertion depth of a rectal temperature probe.

One exemplary depth sensing rectal probe can use two or more temperature sensors, such as thermistors, situated along the length of the rectal temperature probe. At least one sensor situated near or above a ⅝" mark can be used by the thermometer to detect insertion depth. As illustrated by the flow chart of FIG. 14, if the temperature of that sensor rises beyond some pre-set level above ambient temperature, the thermometer can display a warning visual display on the screen, by a light on the probe handle or on the thermometer and/or by a making an audio sound, to warn the operator of an excessive insertion distance. The difference from ambient can be determined, for example, by a sensor in the probe placed well beyond the insertion point.

In all forms of thermometry using a physical contact probe, it is important that there be good contact between the probe and tissue of the body. If the probe to tissue contact is insufficient, the resulting temperature reading can be in error, likely registering too low. In one embodiment of a thermometer including operator error detection according to the invention, a display registering a temperature that is too low, such as too low for a given mode selected, can display an intervention question asking the operator to check if there is good probe-tissue contact. As in other embodiments, the operator can dismiss the medical equipment generated intervention. Immediate dismissal of such an intervention would be appropriate, for example, in the case previously discussed of a hypothermia victim not yet warmed back to a normal body temperature range. Another embodiment of medical equipment that can detect good probe tissue contact can use an additional sensor in the probe. A thermistor is but one example of a temperature sensor suitable for such use. Such additional sensors can also be based on other types of resistance or capacitance sensors in the probe to detect a resistance or capacitance indicating sufficient probe-tissue contact. The additional sensor, in addition to the temperature sensor, can be used for detecting sufficient probe tissue contact. On detection of insufficient contact, one embodiment of medical equipment such as a thermometer, can accomplish a medical equipment generated operator intervention by generating a message on a display notifying the operator of a problem with the probe placement against the body tissue. Such intervention displays can include an image of a same type probe properly situated against a body or in a body cavity. The display can also list common problems and corrective measures for insufficient probe to tissue contact. For example, in some cases it might be necessary to cover a probe with a thermally conductive lubricant to achieve an optimal temperature measurement.

In an oral temperature measurement, as previously discussed, the most common operator error is to not properly situate a temperature probe in the sublingual pocket. However, even where the probe has been correctly placed by the operator in the sublingual pocket, another problem can still cause an inaccurate temperature measurement result. If the person bites down on the probe, typically with their teeth, but even using gums alone without dentures, the probe can be moved, there can be excessive probe motion, or the lips can be opened during biting causing an erroneous reading. In one embodiment, a measurement too low for a selected mode can cause one of a list of possible problems to include probe biting. In a more sophisticated embodiment, the temperature probe can include a biting sensor in addition to a temperature sensor. The pressure sensor can be an internal probe contacts that close with sufficient external biting pressure. Or, the accelerometers, previously discussed as position sensors, can detect excessive temperature probe motion caused by biting. Alternative biting detection sensors including detecting a higher pressure in a flexible tube probe having a hollow section or a change in electrical parameter, such a temperature probe comprising a material that changes resistance or capacitance with biting probe pressure. In an embodiment having a temperature probe including a biting sensor, a medical equipment intervention can specifically alert the operator to the specific biting problem, without need for further operator troubleshooting.

Non-Invasive Blood Pressure Measurements:

We now describe several embodiments of the inventive system and method as applied to non-invasive blood pressure (NIBP) measurements. A non-invasive blood pressure measurement is generally performed using a blood pressure cuff.

Example 8

Figure 15:
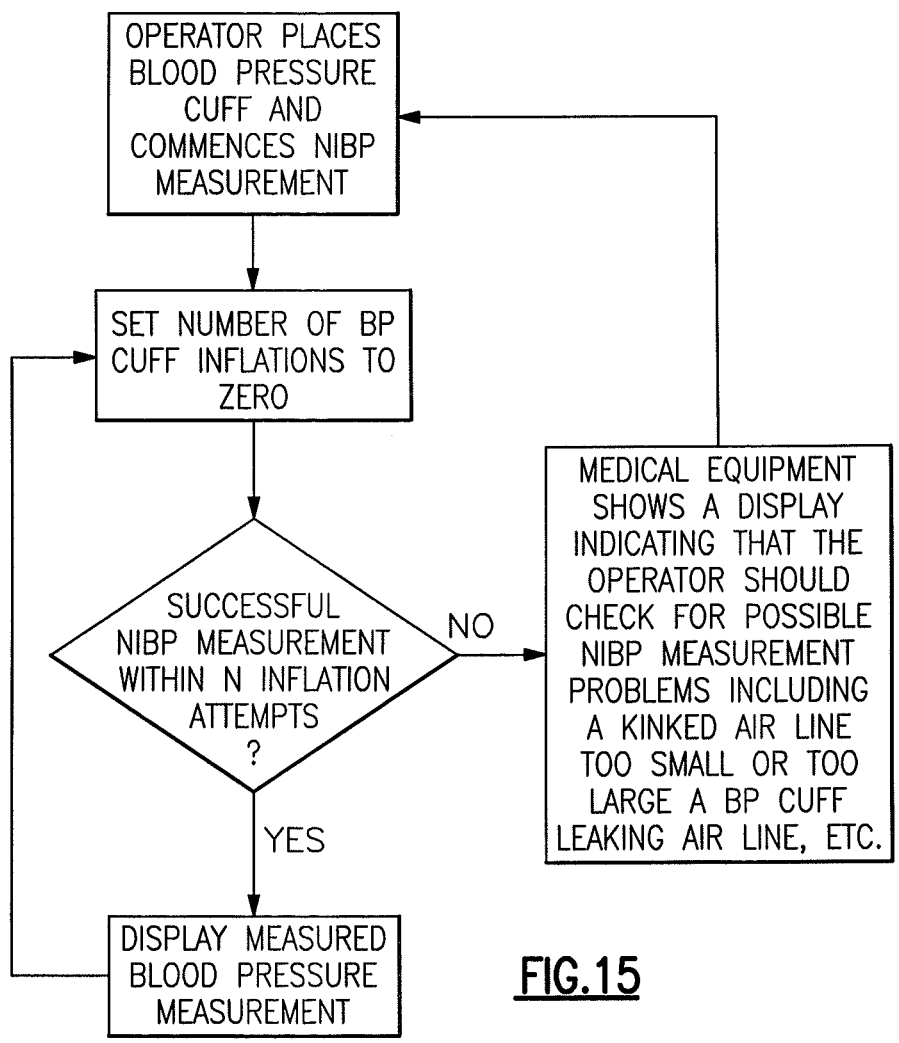
FIG. 15 shows a flow chart illustrating a non-invasive blood pressure monitor offering in-service help where there has not been a successful NIBP reading taken within N inflation attempts.

In automatic blood pressure measurements, typically one or more bladders are inflated by air pumps controlled by the medical equipment. The blood pressure of a person is typically determined using a pressure sensor according to an oscillometric method. Most equipment using an air pump, automatically tries another bladder inflation following an unsuccessful reading. In one embodiment as illustrated by the flow chart of FIG. 15, the number of re-tries can be used as an additional parameter to generate a medical equipment intervention. If the number of retries between successful readings exceeds a predetermined number, the medical equipment can display an operator intervention display. The display can indicate that there have been too many inflations associated with attempts by the medical equipment to make a valid blood pressure measurement. The display can also indicate possible reasons, such as kinked air line to the bladder in the cuff, too small or too large a cuff for the person being monitored, a leaking air line, or other similar fault that could be creating the problem. The operator can correct the problem, preferably by attention to one of the displayed list or displayed images of likely potential faults. Following the correction, the medical equipment can close the intervention screen and resume normal blood pressure measurements. It should be noted that equipment using manually inflated non-invasive blood pressure cuffs can use a similar medical equipment intervention system by incorporating a sensor to monitor manual inflation cycles. While such error detection is probably most practical when configured in automatically inflated cuff systems, an inline pressure sensor or automatic valve position sensor could provide such an inflation count for manually inflated cuffs. Similarly, other indicators of wrong cuff size, too loose or too tight a cuff, or kinked or leaking air hoses can be used to generate intervention displays.

Example 9

Figure 16:
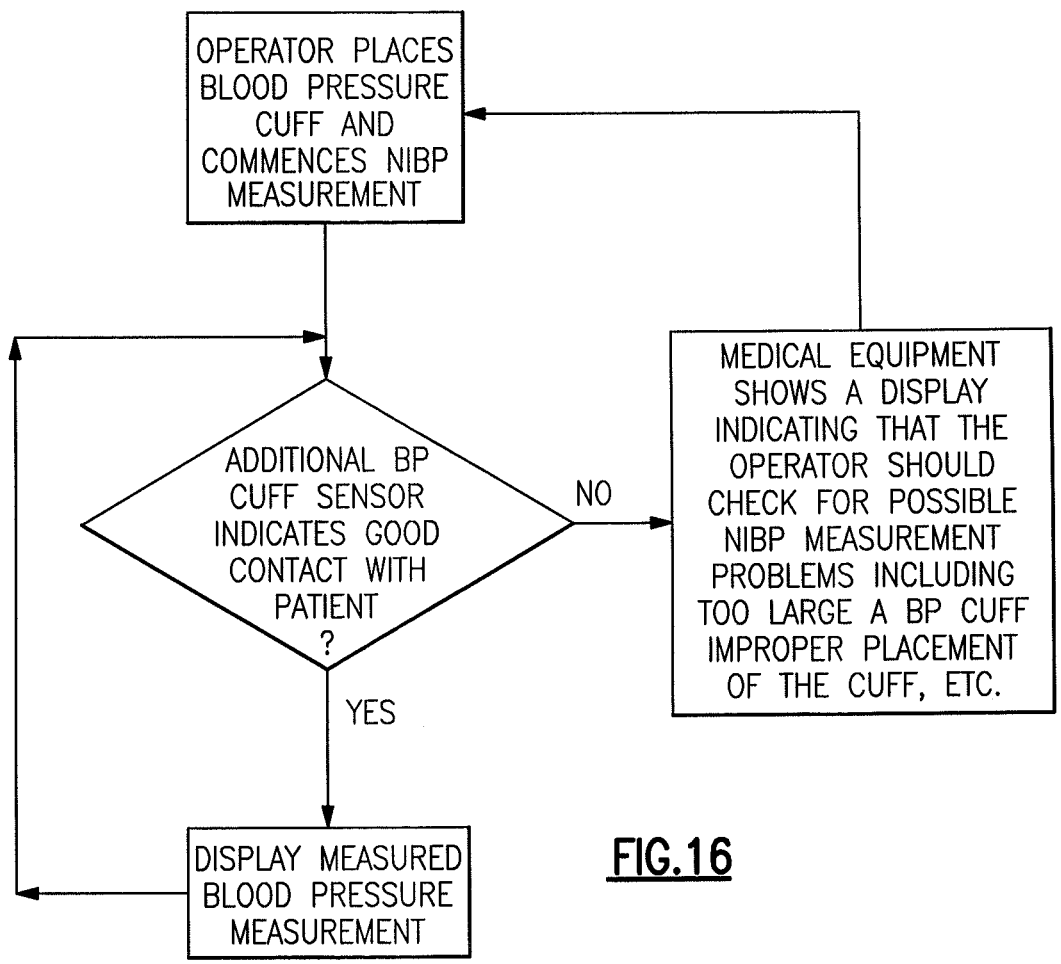
FIG. 16 shows a flow chart illustrating a non-invasive blood pressure monitor offering in-service help where there has not been good contact by the NIBP cuff with a person's limb.

One common operator error pertains to loss of contact of the cuff to the surface of a limb of the person to which the cuff is affixed. For example, if the cuff size is inappropriately large for the limb it is affixed to, there can be insufficient contact. In a non-invasive blood pressure measurement according to the invention, one exemplary embodiment can have an additional sensor, such as a thermistor temperature sensor, installed on a surface of the cuff intended to come in contact with the limb, typically a person's upper arm. As in other embodiments, and as illustrated by the flow chart of FIG. 16, an operator activates and sets up the medical equipment, such as a blood pressure monitor or equipment having a blood pressure measurement as one of a plurality of medical measurements. The equipment begins to read the blood pressure measurements from a non-invasive blood pressure cuff affixed to a limb of the person. Both the blood pressure data and/or the thermistor data can be analyzed by an algorithm running in conjunction with the medical equipment. Typically the algorithm is running on a microcomputer that is a part of the medical equipment. If the medical equipment detects a temperature read from the thermistor in the cuff that is below what would be expected as a surface temperature measurement on the person, the equipment can intervene. The equipment can advise the operator, typically by a display of text and/or images, that there is insufficient contact between the cuff and the person's limb. The display can include a number of possible causes, including for example, improper placement of the cuff, or that the cuff size might be too large for the person's limb size. The operator can take corrective action by re-attaching a properly sized cuff more snuggly to the limb, or by replacing the cuff with a smaller cuff size. Following the remedial action by the operator, the thermistor in the cuff registers a temperature that is within limits indicating proper contact with the person's limb. The equipment removes the warning or error display and proceeds with an error free non-invasive blood pressure measurement. Following an automatic detection of one or more of the aforementioned operator errors, a help screen can be offered or automatically displayed (as positive intervention by the equipment) to provide the operator with recommendations (to correct and solve the problem). For example, in the case of the wrong cuff placement, a displayed picture or image can illustrate where the clinician should line up the antecubital in addition to providing instructions on how to place the cuff snugly around the patient's arm. Another image can show an Operator how to determine if the instrument detects that the cuff they have is too big or too small for the patient's arm. In some embodiments, an operator can be offered a brief list of possible problems to choose from. Or, in other embodiments, the medical instrument can make a best estimate of the problem and offer the remedial image for that problem, while offering operator selectable alternatives on the same screen, such as by active screen buttons or displayed labels next to definable hardware buttons.

ECG Measurements:

Turning to ECG measurements, the inventive system and method can be used to allow medical equipment to identify and intervene in a number of different types of ECG measurement errors. In a most basic solution, the ECG equipment or EGG section of a more general medical monitor, can process ECG measurements and identify by an error detecting algorithm that one or more ECG probes are missing or incorrectly placed. One method for this determination is to compare expected signal levels and polarity and/or signal phase from lead to lead for the given type of ECG probe number and placement expected. Where the electrical signals from the respective electrodes does not match the parameters of the basic signal expected, the medical equipment can display an intervention display. The display can note missing signals (including electrodes that have fallen off the person) or incorrectly placed electrodes and suggest likely causes and corrective measures. For example, where a signal is missing for a 5 electrode measurement, the equipment can display the location of the missing electrode and prompt for proper placement of that electrode, re-placement of the electrode, or setting an ECG mode for a smaller number of electrodes, if that was what the operator intended (i.e. a probe is not missing or in poor contact, however the ECG medical equipment mode was set to an incorrect mode, such as a mode expecting more electrodes). As with other equipment interventions according to the inventive system and method, it can be helpful to display the intervention screen as an image, here showing expected electrode probe placements on a body and a notation showing which electrode signals are missing or yielding an electrical signal different from that expected for a properly placed electrode. Also, most intervention displays according to the invention can also include an operator escape path, including such options as "okay", "ignore", or "change mode" to dismiss a particular intervention display.

Example 10

Figure 17:
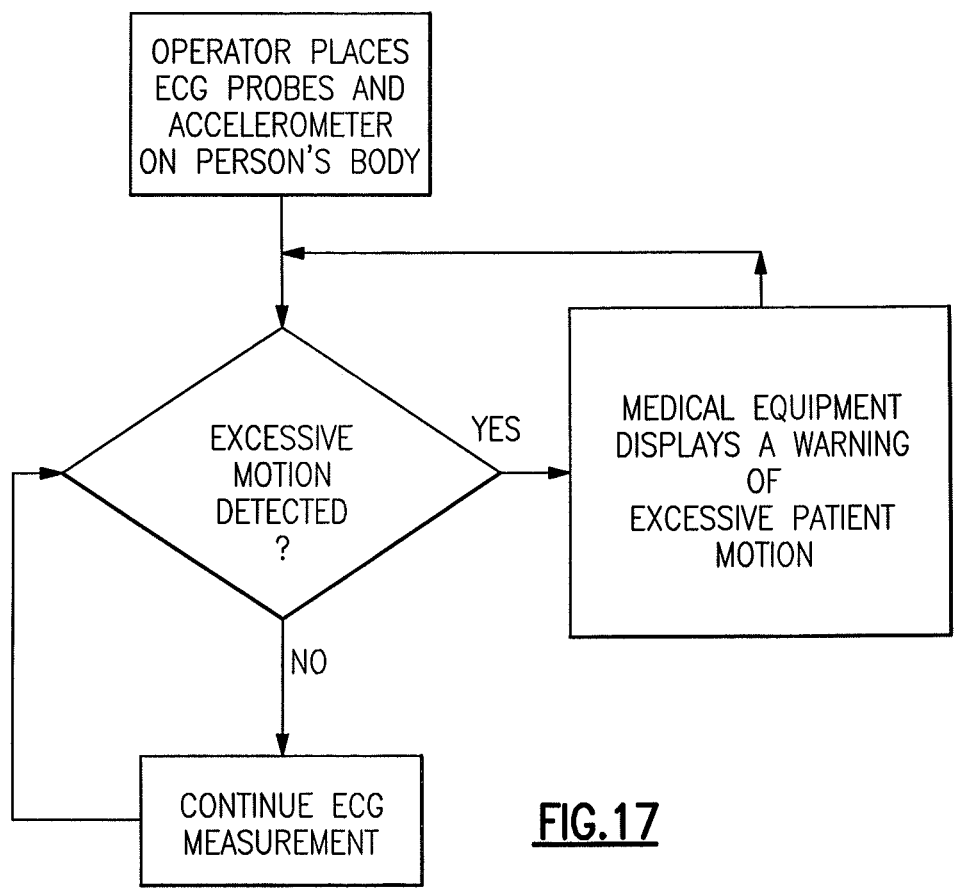
FIG. 17 shows a flow chart illustrating an ECG monitor offering in-service help where excessive patient activity has been detected by a motion sensor such as one or more accelerometers.

Another potential problem associated with ECG measurements is ECG artifact signal, typically associated with poor electrode placement or excessive patient motion. As before, the medical equipment can identify poor electrode connections, such as a loose or defective electrode in part by the electrical signal measured at each electrode. However, it can be more difficult to determine the cause of artifact error by electrode signals alone. Medical equipment making ECG measurements can use an additional parameter to assist in artifact error identification. For example, as illustrated by the flow chart of FIG. 17, in addition to electrodes, an accelerometer can also be affixed to a person undergoing an ECG measurement. Here, in addition to measuring and evaluating the electrical signals from the ECG electrodes, the medical equipment can also measure analog or digital electrical signals from an accelerometer. The artifact error detection can be based on a combination of the physiological (ECG) signals and the output of the accelerometer or on the accelerometer alone. If the accelerometer indicates excessive motion of the person for the given ECG type measurement selected, the medical equipment can generate a display indicating excessive patient motion. The operator can attempt to stabilize the person in response to the display, such as by talking to the person where the motion can be controlled by the person, administering other corrective actions such as better bed support for the person or slightly repositioning the person. When the undesired motion as measured by the accelerometer has sufficiently subsided, the intervention display goes away and the ECG measurement can resume. The excessive motion information, such as from an accelerometer, can be recorded with the ECG data to help interpret the results at a later reading of the FCC data.

Example 11

Figure 18:
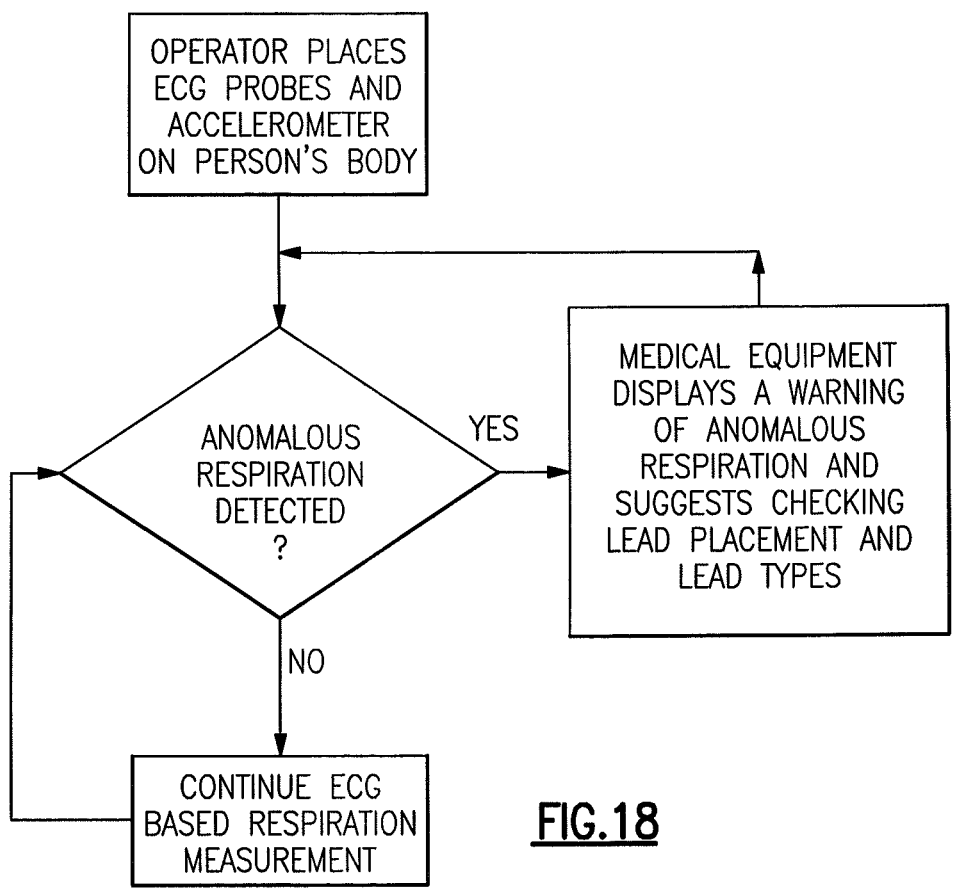
FIG. 18 shows a flow chart illustrating an ECG monitor that detects respiration, offering in-service help where anomalous respiration readings have been detected.

Respiration can be detected from ECG measurements. In some cases, such as due to incorrect lead placement or selection of the wrong lead types, these ECG respiration measurements can be in error. As illustrated by the flow chart of FIG. 18, following a detection of erroneous respiration measurements, the medical equipment can display an intervention screen that illustrates a correct ECG lead placement. For example, if they are in a lead 1 (RA to LA) configuration, but the patient is a belly breather, a displayed intervention image can recommend a change the lead to ECG 2 which is a LA to LL configuration.

$SPO_2$ Pulse Oximetry Measurements:

$SpO_2$ pulse oximetry measurements of blood-oxygen saturation are also subject to a number of operator errors. Some of the most common errors include not using the correct probe or improper probe placement.

Example 12

Figure 19:
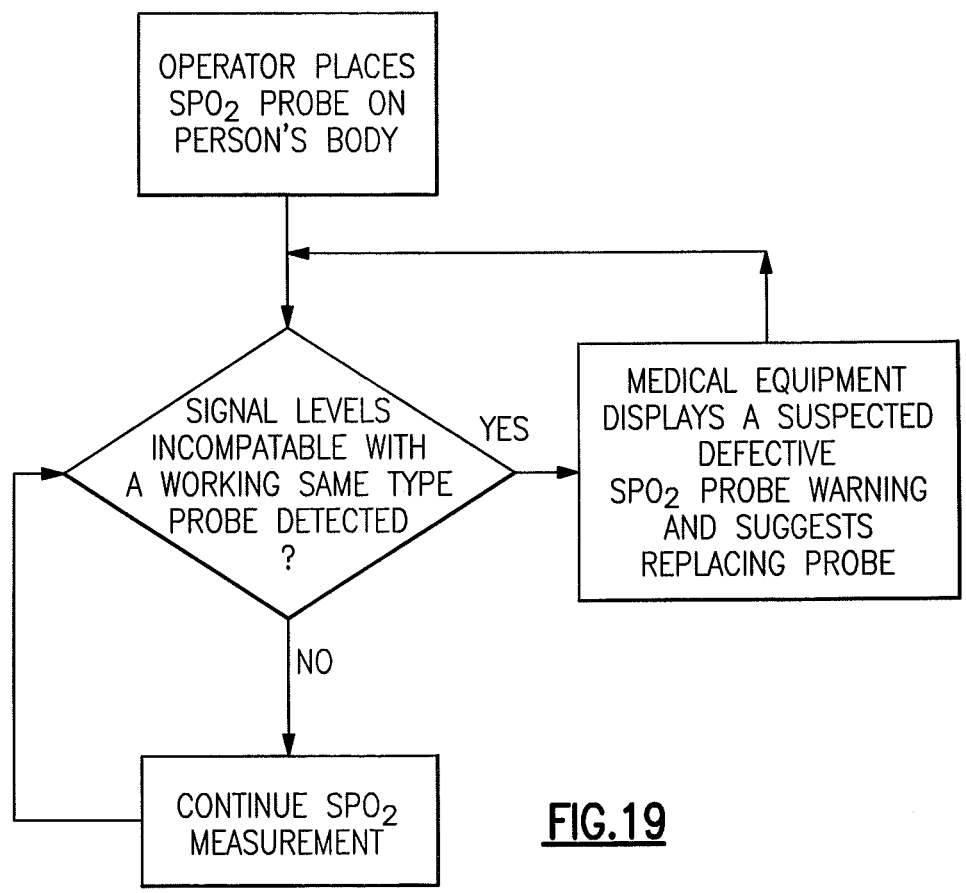
FIG. 19 shows a flow chart illustrating a $SPO_2$ monitor, offering in-service help where signal levels are inconsistent with a selected probe type.

In one embodiment, as illustrated by the flow chart of FIG. 19, the medical equipment can detect an improper or defective probe by use of suitable electronic circuitry and/or an algorithm to compare measured results to expected valid signals from a comparable working $SPO_2$ probe. Generally in the case of a defective or incompatible probe, the measurements will be very far from expected in one or another direction, or in the case of electronic circuit detection, the incorrect or defective probe will have electrical characteristics, such as current draw, voltage levels, or signal timing, very different from that which is expected by the medical equipment. In such cases, the medical equipment can display text and/or an image describing the problem, a suspected incorrect or defective probe and suggest replacement of the probe. Following attachment of an operable suitable $SpO_2$ probe, the intervention display can be removed and replaced by a normal display of desired medical parameters.

Example 13

Figure 20:
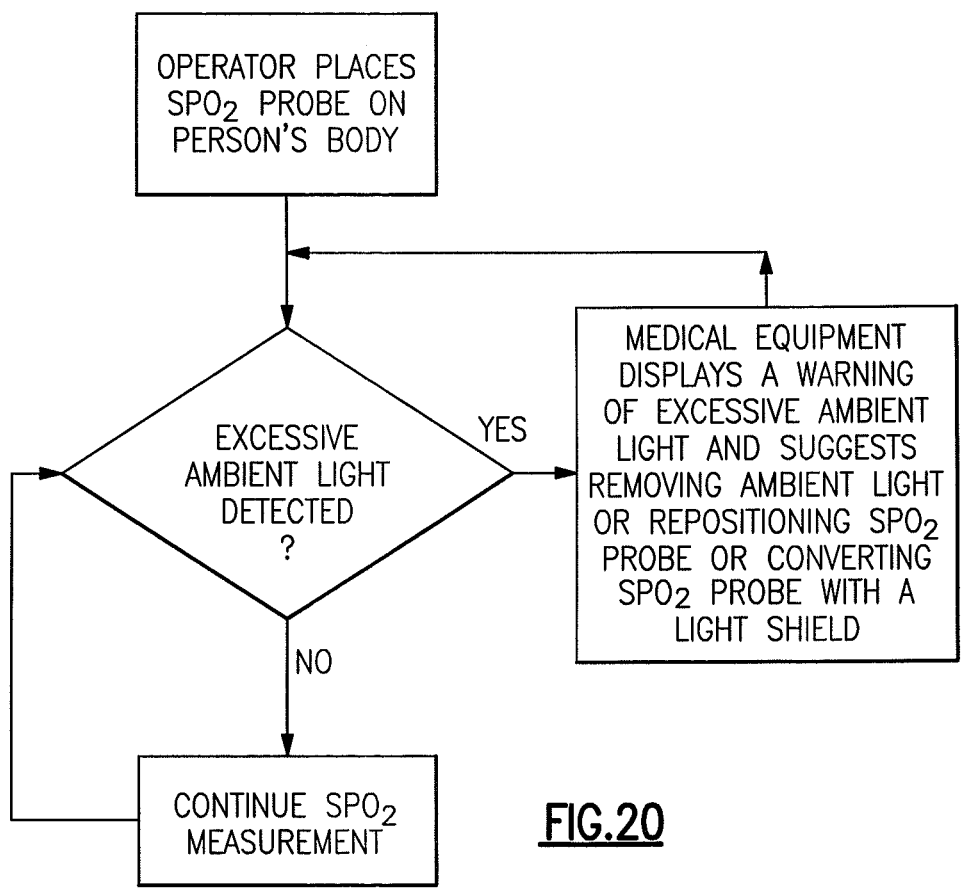
FIG. 20 shows a flow chart illustrating a $SPO_2$ monitor, offering in-service help where excessive ambient light has been detected as the $SPO_2$ probe.

In another embodiment, an operable suitable $SpO_2$ probe is properly connected to the medical equipment and the probe is apparently good, however an error detecting algorithm indicates improper, e.g. out of range, $SpO_2$ measurement data. The medical equipment can present a display indicating the $SpO_2$ error and suggesting possible operator remedial actions most likely to yield a correct $SpO_2$ measurement. In various related embodiments, there can be additional sensors in the $SpO_2$ probe and additional sensor outputs from the $SpO_2$ probe to help the medical equipment determine the source of error. For example, as illustrated by the flow chart of FIG. 20, one or more light sensors built into or situated on a surface of the $SpO_2$ probe can be read by the medical equipment to determine if there is too much ambient light for the $SpO_2$ probe to function correctly. Since most $SpO_2$ probes use an electro-optical system that measures light transmission through tissue, too much ambient light can interfere with a normal measurement by saturating a light sensor used in the $SpO_2$ measurement circuit. In some cases it might be possible to achieve dual use of the $SpO_2$ measurement circuit light sensor for sensing excessive ambient light as opposed to incorporating an additional ambient light sensor. Following an excessive ambient light detection, the operator can remove the source of ambient light or reposition the sensor away from the ambient light, or cover the sensor with a light shield. Once the medical equipment sensor used for ambient light determination senses that the problem of excessive ambient light is no longer present, the intervention display can be removed and a normal display of medical measurements can be presented by the medical equipment to the operator.

Where the medical equipment detects an improper probe placement, a picture can be displayed that illustrates how to properly place the probe on the finger. For example, a picture can show an operator how to place the wire on top when using a Nellcor reusable probe. The same image, or a subsequent image, can provide additional helpful operator advice, such as, "Do not place the probe on the same arm as the BP cuff as such placement can cause alarms during every inflation". Instructional displays can include a help menu, such as a drop down menu that allows an operator receiving medical equipment intervention assistance to choose a type of probe they are using, such as a Nellcor probe or a Masimo probe, in addition to the type of probe such as a finger probe, forehead probe, etc.

Example 14

Figure 21:
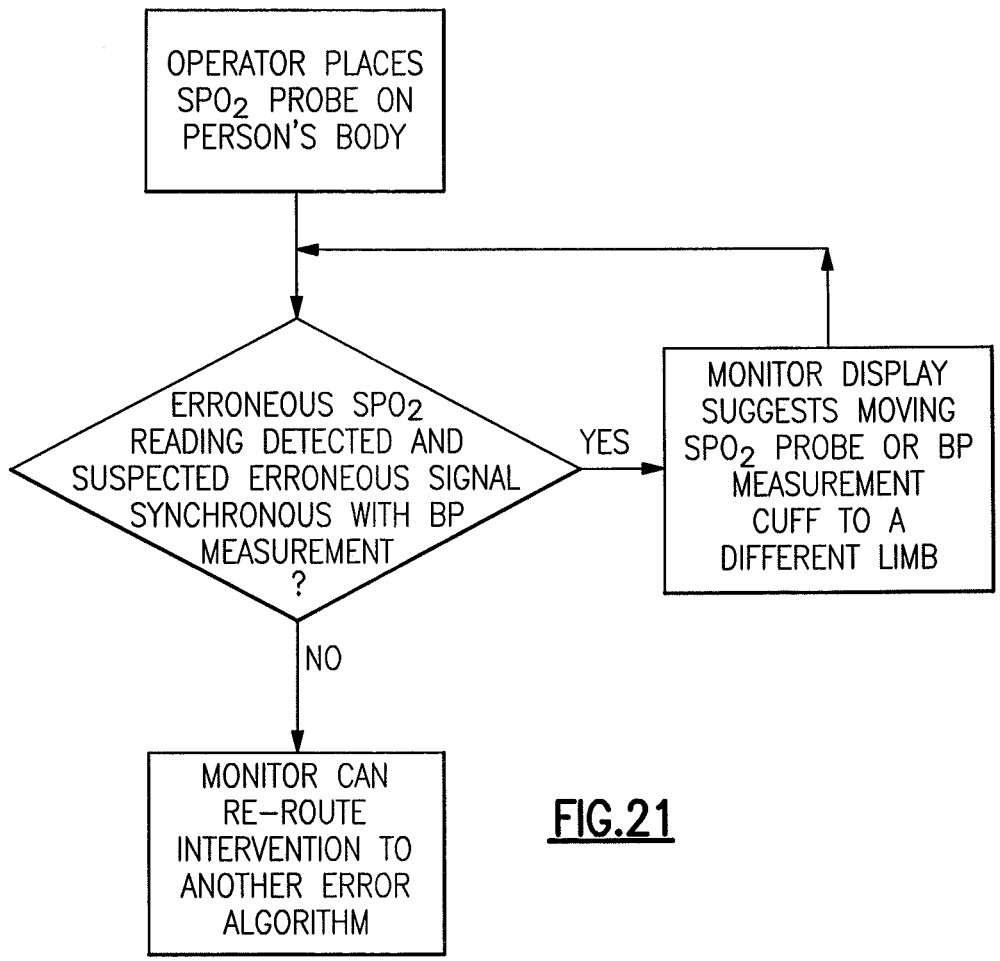
FIG. 21 shows a flow chart illustrating a $SPO_2$ monitor, offering in-service help where an erroneous $SPO_2$ reading is correlated to a NIBP cuff on the same limb.

In another embodiment of operator error detection and correction by medical equipment as illustrated by the flow chart of FIG. 21, an $SpO_2$ probe has been placed on the same arm as is being used for a non-invasive blood pressure measurement. An error detecting algorithm running on the medical equipment detects an erroneous $SpO_2$ measurement. In medical equipment, such as a medical monitor, that performs both the non-invasive blood pressure measurement as well as the $SpO_2$ measurement, the error detecting algorithm can accept inputs from multiple measurements. The algorithm can recognize that the $SpO_2$ measurement error always occurs in synchronization with or at the same time as, for example the blood pressure cuff inflation cycle. Here, the medical equipment can intervene and display text and/or an image showing an error caused by having the blood pressure cuff on the same limb as being used for the $SpO_2$ measurement. The operator can move either the $SPO_2$ probe or the blood pressure cuff to another limb. On recognizing that there is no longer an erroneous $SpO_2$ measurement, the medical equipment can remove the intervention display and return to a desired display screen, such as the display format in use when the error was detected.

Example 15

Figure 22:
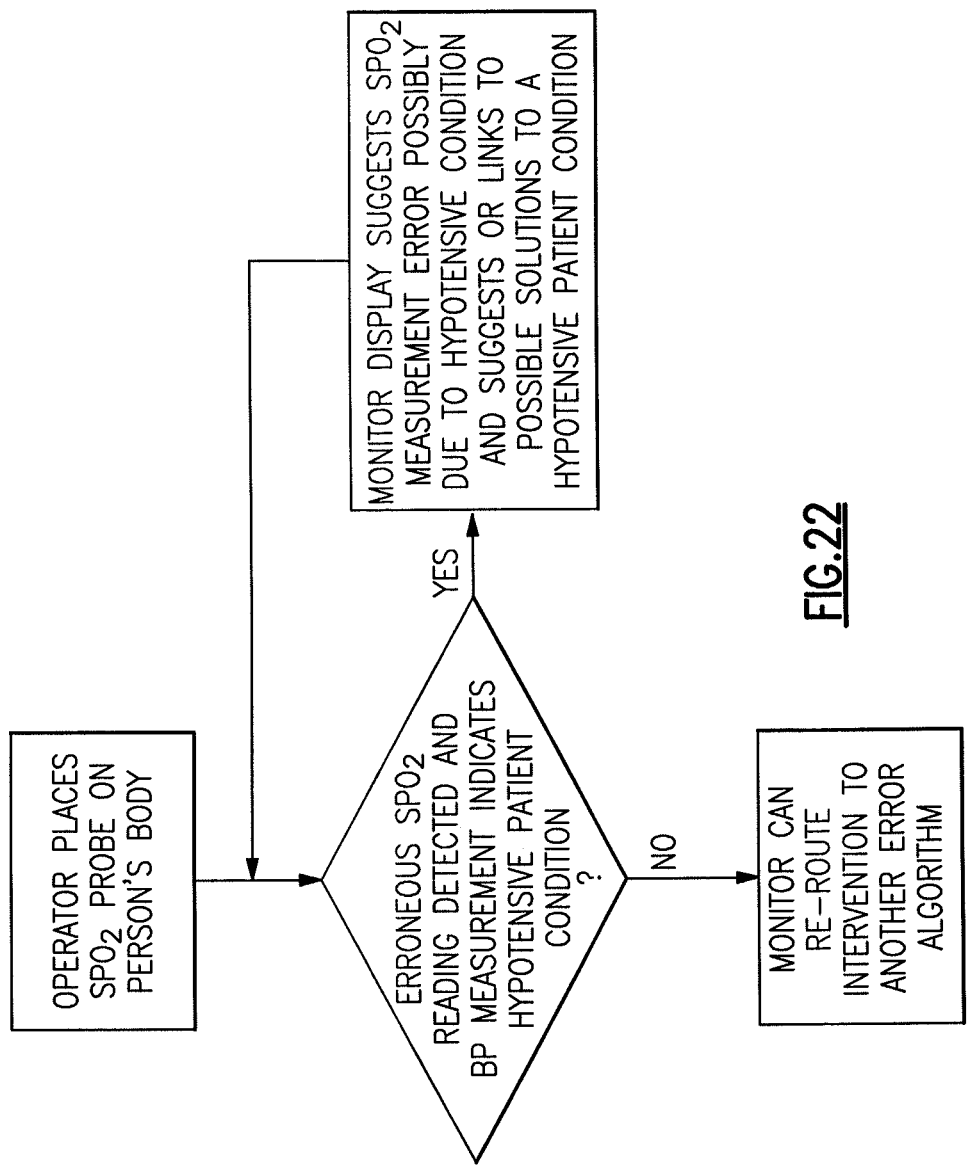
FIG. 22 shows a flow chart illustrating a $SPO_2$ monitor, offering in-service help where an erroneous $SPO_2$ reading is correlated to a hypotensive patient condition.

In another embodiment of operator error detection and correction by medical equipment, as illustrated by the flow chart of FIG. 22, an $SpO_2$ probe has been correctly placed. The $SpO_2$ measurement is still in error. The medical equipment, also including a blood pressure measurement includes an algorithm to evaluate the blood pressure measurement as a second parameter when evaluating $SpO_2$ measurements. While the $SpO_2$ measurement is in error, the medical equipment determines from the second blood pressure parameter that the cause of the erroneous $SpO_2$ measurement is most likely that the person is hypotensive. An intervention display alerts the operator to the $SpO_2$ measurement error and displays a screen that addresses solutions to the person's hypotensive condition, the most likely cause of the $SpO_2$ measurement error.
Capnography Measurements:
Capnography is a non-invasive method for monitoring the level of carbon dioxide ($CO_2$) in exhaled breath to assess a person's ventilatory status. A capnograph can produce an $EtCO_2$ value as well as a waveform, or capnogram. Capnography can be used for monitoring ventilator status, warning of airway leaks and ventilator circuit disconnections, and ensuring proper endotracheal tube placement. Since capnography is a less used measurement, any intervention displays can also include an option to view a normal $CO_2$ waveform. There can be more than one normal waveform, such as normal or typical waveform for various patient conditions or various types of medical equipment being used to assist and monitor a person.

Figure 23:
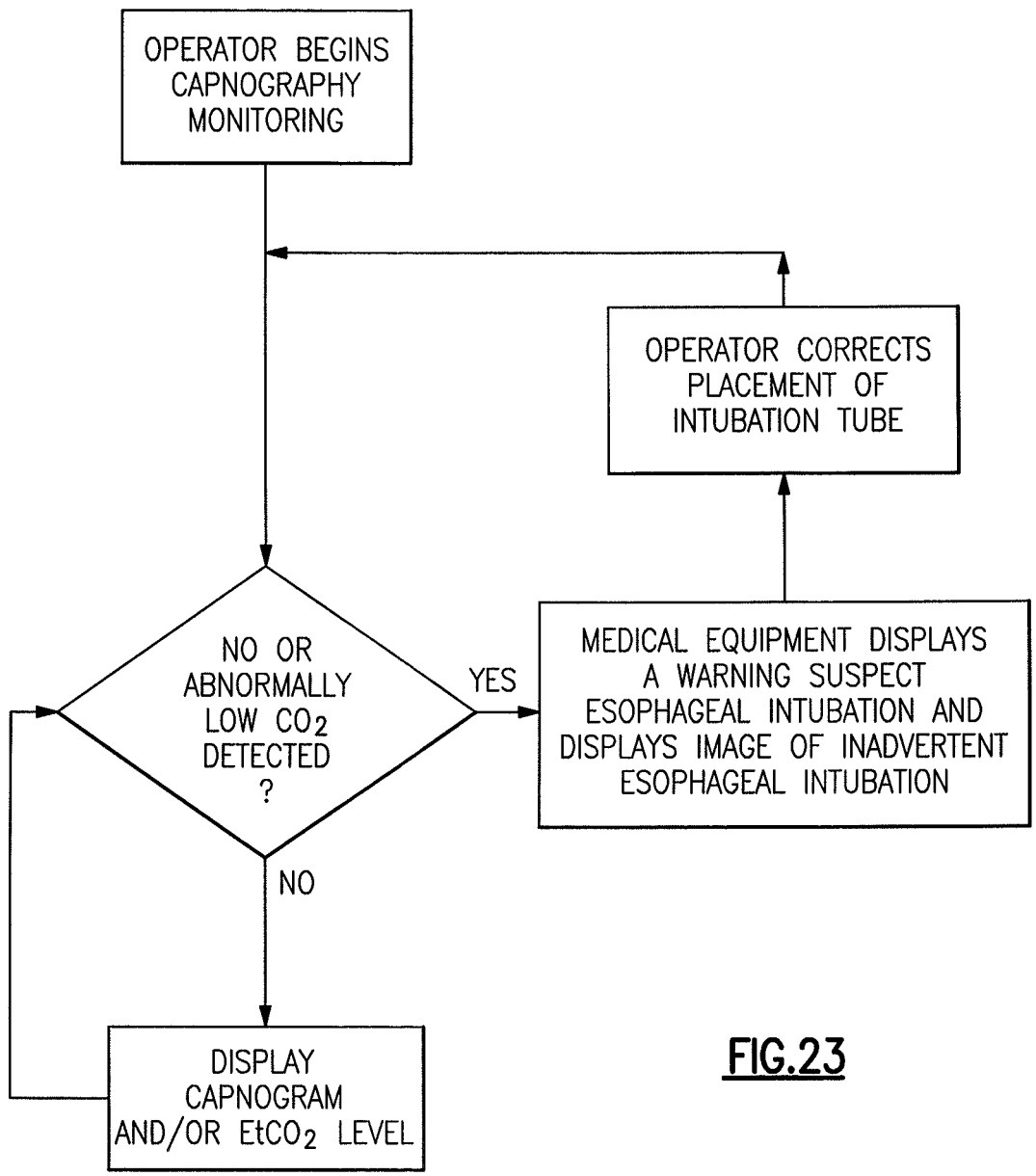
FIG. 23 shows a flow chart illustrating a $CO_2$ monitor, offering in-service help where no or abnormally low $CO_2$ levels are measured.

Example 16

Where no $CO_2$ is measured and/or only small short capnograms are being displayed on a monitor, as illustrated by the flow chart of FIG. 23, a warning, such as "suspect an esophageal intubation" should be displayed in addition to recommending an immediate intervention. One or more displayed images can show a correct intubation or a correct intubation next to an image of an inadvertent esophageal intubation. Following correction by the operator, and monitoring of a more nominal capnogram, the intervention display can be suspended.

Example 17

Figure 24:
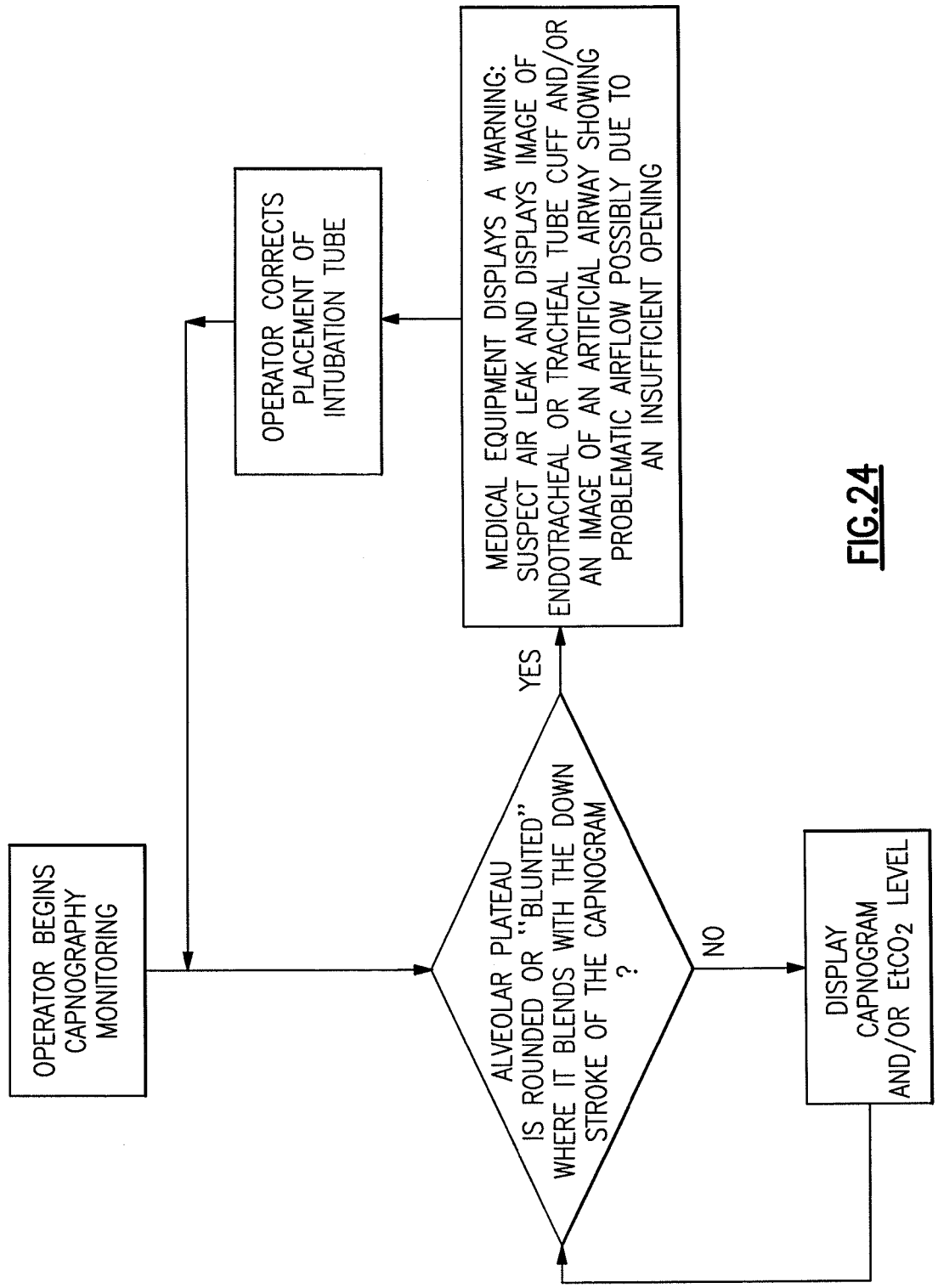
FIG. 24 shows a flow chart illustrating a $CO_2$ monitor, offering in-service help where the alveolar plateau is rounded or "blunted" where it blends with the down stroke on the corresponding capnogram.

If the alveolar plateau is rounded or "blunted" where it blends with the down stroke of the capnogram as displayed on the monitor, as illustrated by the flow chart of FIG. 24, there can be a display with the warning message "suspect air leak". Displayed images can be of an endotracheal or tracheal tube cuff and can include recommendations to check the endotracheal or tracheal tube cuff and/or images of the artificial airway can graphically show problematic air flow where the artificial airway is too small for the person.

Example 18

Figure 25:
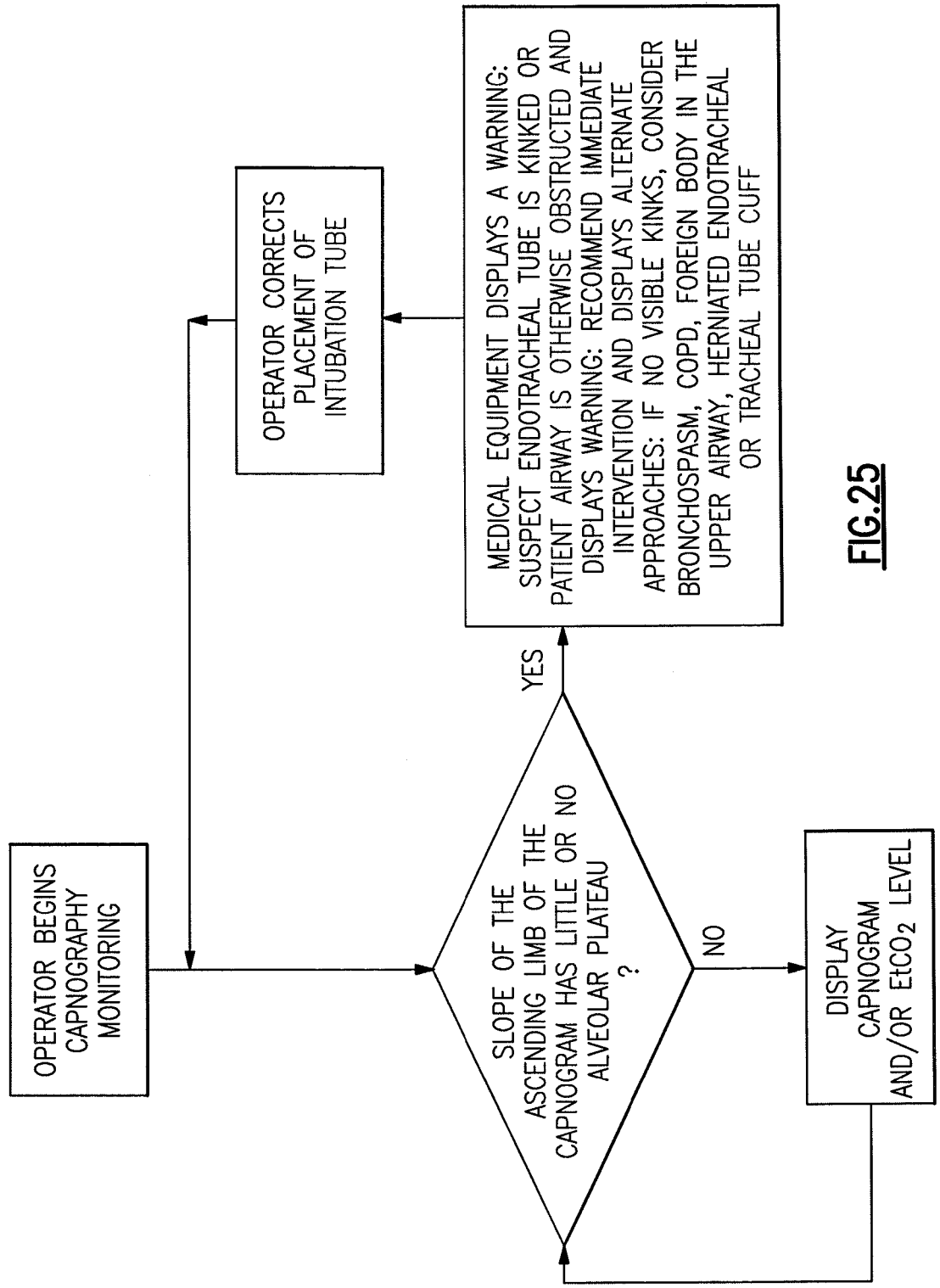
FIG. 25 shows a flow chart illustrating a $CO_2$ monitor, offering in-service help where the slope of the ascending limb of the capnogram having little or no alveolar plateau on the corresponding capnogram.

If the slope of the ascending limb of the capnogram having little or no alveolar plateau is being displayed on the monitor, as illustrated by the flow chart of FIG. 25, a displayed image can be accompanied by the warning "suspect endotracheal tube is kinked or patient airway is obstructed, "RECOMMEND IMMEDIATE INTERVENTION" (the latter part of which can be emphasized in any combination of font style, size, color and background color). The displayed image can show additional notes such as, "If no visible kinks, consider bronchospasm, COPD, foreign body in the upper airway, herniated endotracheal or tracheal tube cuff". Additional images further describing or illustrating a bronchospasm, COPD, foreign body in the upper airway, herniated endotracheal or tracheal tube cuff can be included or linked to the initial intervention display by operator selections.

Example 19

Figure 26:
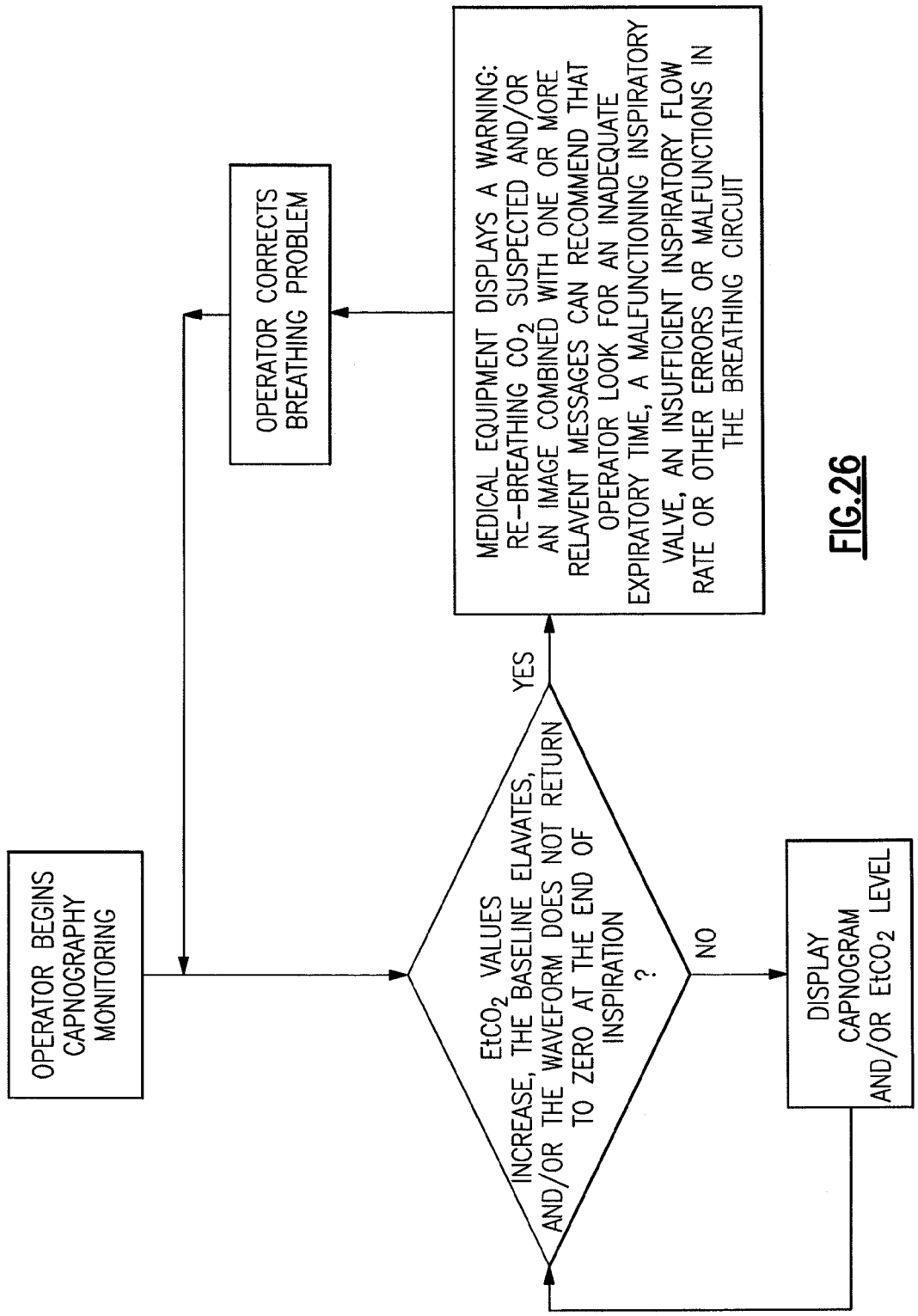
FIG. 26 shows a flow chart illustrating a $CO_2$ monitor, offering in-service help where the $EtCO_2$ values increase, the baseline elevates, and/or the waveform does not return to zero at the end of inspiration is being displayed on the corresponding capnogram.

If the $EtCO_2$ values increase, the baseline elevates, and/or the waveform does not return to zero at the end of inspiration is being displayed on the monitor, as illustrated by the flow chart of FIG. 26, there can be a displayed warning "Rebreathing $CO_2$ suspected". A display combined with one or more relevant images can recommend that the operator look for an inadequate expiratory time, a malfunctioning inspiratory valve, an insufficient inspiratory flow rate or other errors or malfunctions in the breathing circuit.
Medical Equipment Evaluation and Advice:
In another embodiment of the invention, a medical instrument can be programmed to evaluate readings of physiological parameters and to provide recommended or required actions based on those readings. Such actions can be based on presently accepted good medical practice and/or local protocols and policies of a particular medical facility such as a particular hospital. The recommendations for action can be made, for example, via a text or video display situated on or in the equipment so as to be visible to a clinician operator.

Example 20

Figure 27:
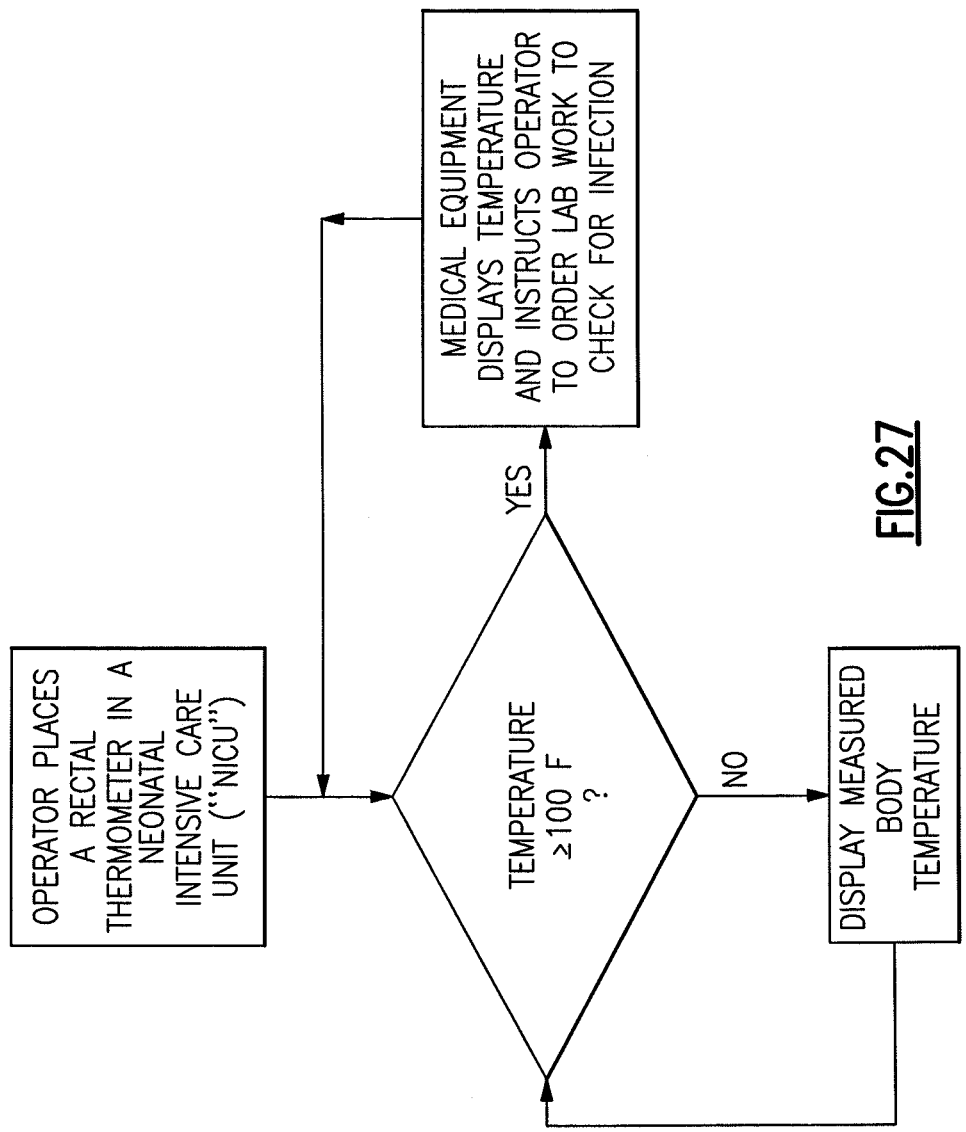
FIG. 27 shows a flow chart illustrating a thermometer offering in-service help related to a medical testing protocol where the readings are over 100° F.

A thermometer used in a hospital clinical setting can include notices that appear on the thermometer display screen advising of required tests when a patient's temperature exceeds certain limits. For example, as illustrated by the flow chart of FIG. 27, a rectal thermometer in a neonatal intensive care unit ("NICU") can be programmed to order lab work to check for infection when an infant rectal temperature is measured by the thermometer at 100 degrees F. or higher. Such diagnostic protocol advice can be prompted by, for example, manual operation of a "measure button" on the thermometer. The advice can be in the form of a text message on the same screen that displays the temperature reading or in some other format or on some other display screen or page. In some embodiments, a clinician can be prompted, such as by a menu option, to request a display of recommended or required actions based on a certain temperature reading.

"Rules" for determining proper values or expected time-physiological curves or recommended or required actions can be stored locally on the hardware of the medical instrument. We define rules as including any instructions, procedures, physiological profile curves, procedures or protocols. These rules can be programmed in software or firmware or in a combination of software or firmware. For example, rules can be stored in memory 107 of FIG. 1A or in memory internal to microcomputer 105 as represented by data profile 108. In other embodiments, rules can be stored on another computer, computer server, or memory, all of which can be external to the medical equipment. Memory, such as memory 107 of FIG. 1A or memory in addition to memory 107 (not shown in FIG. 1A) can include removable memory media ranging from a plug in memory card, memory stick, a USB memory device, or disc based media including DVDs, CDs, and hard drives.

Where rules are external to the medical equipment, the medical equipment can load some or all of the rules on "turn on" or "boot up", or some or all of the rules applicable to a certain type of equipment or certain type of measurement can be queried following each measurement. In the latter case, an additional benefit is that rules can be applied universally to specific types of clinical measurements without regard to the model, or manufacturer, of the medical equipment in use. Rules can be communicated to and from medical equipment by wired or wireless technologies. Suitable wireless connections include, but are not limited to, WiFi, Bluetooth, WiMAX, and cellular network connections.

Training Modes:

Returning to medical equipment in general, we also note that an in-service or training mode can be actuated by an external key such as an RFID fob in the form of a "key fob", such as used as an authentication token, or a magnetic card. The medical instrument, such as a thermometer or medical monitoring unit, can then be used as a training aid which would walk the inexperienced clinician through the vital signs process. A key fob or other suitable type of authentication token can also be used to run a medical equipment calibration process.

Each training mode can be customized by configuration software where each clinic or hospital can set thresholds on various measurement error codes, such as blood pressure error codes or thermometry error codes. For example, if a temperature measurement is attempted without a probe cover, where a medical instrument can detect the presence of a probe cover, an in-service video or warning could appear prompting a clinician operator to run the instructional program.

Where service training is available, there can also be an option to manually call for operator assistance at the prompting of an operator or training supervisor, as opposed to waiting for the medical equipment to automatically present operator advisory images. In such training case, particularly where a simulated display is shown for training purposes such as on vital signs monitoring medical equipment, there can be a warning, such as a flashing light or on-screen notice, that a training sequence is being displayed. Such training can be done simultaneously with continued vital signs monitoring by the medical equipment, including active data transmission of actual measured physiological data to other monitoring stations and active internal alarm monitoring of the actual physiological data still being monitored while the medical equipment might be displaying a training sequence, Medical equipment training information and video can also be stored on and supplied to the medical equipment by wired or wireless connection to computer or computer server. The computer can be a standalone computer or a computer on a computer network. For example the medical equipment can be connected via a standard USB port to a personal computer (PC). The PC can then download particular training sequences to the medical equipment for later use or on demand to satisfy a particular training request. By downloading training sequences from other computers or computer networks, there is less need for a large memory in the medical equipment. Also, it is easier to maintain a latest approved set of uniform and consistent medical equipment advisory information, rules, and training files in each clinical setting.

We also note that while the inventive system and method is particularly helpful to reduce medical equipment operator errors by providing active intervention by the medical equipment, such medical equipment advisory actions can also be helpful in routine medical equipment servicing situations. Such service situations can include routine maintenance tasks, such as how to re-load paper or to disinfect the unit.

Example 21

Figure 28:
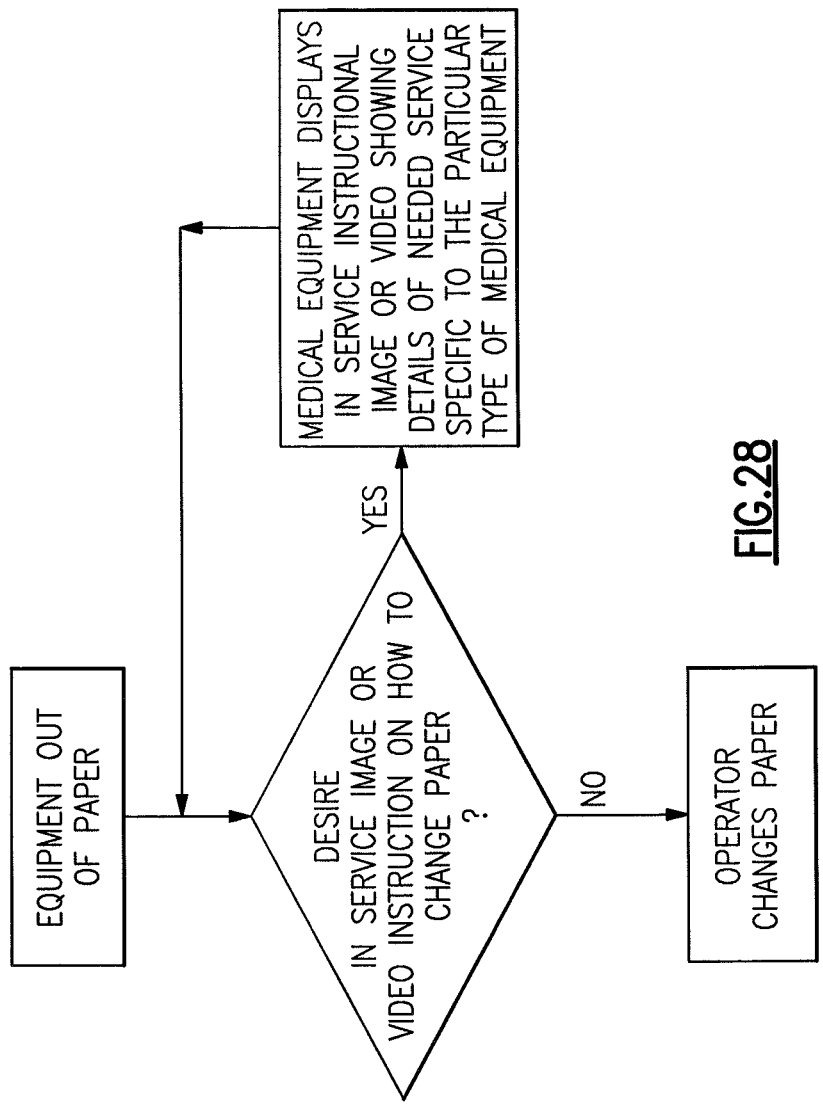
FIG. 28 shows a flow chart illustrating medical equipment offering in-service help on how to service a particular monitor model type.

An out of paper detection can cause an equipment intervention, as illustrated by the flow chart of FIG. 28, that offers the operator an in-service video or image, or the equipment can automatically run an in-service video or image to help an operator understand by demonstration how to change the paper. Similarly, a paper jamb indication can cause an equipment intervention that offers the operator an in-service video or image, or the equipment can automatically run an in-service video or image to help an operator understand by demonstration how to un-jamb the paper feed path. Other in-service difficulties that can be addressed including routine electrical power and communications difficulties. Such other in-service difficulties can range from a low battery indication to a wireless medical instrument out of range of the wireless network, where in-service help can suggest how to reconnect to a network.

Operator Access Controlled by Training Records:

In some cases, it can be desirable to restrict operator access to medical equipment, or to certain medical equipment modes or operations. For example, only to those operators specifically trained on a particular type of medical equipment are allowed access to operate that equipment type. In some embodiments, lesser trained individuals can be permitted to display readings, settings, or measurement results in various equipment modes, but not to change equipment settings and parameters without a higher level access based on training records. In one embodiment, the medical equipment can control or allow access or levels of access by requiring identification of the operator. Identification can be performed by any identification method as known to those skilled in the art, including bar code or magnetic stripe reading of an ID card, wired or wireless recognition of a key fob or other carried ID module including, for example, RFID techniques, or by simply entering an ID number or alphabetic sequence, such as by keypad or keyboard.

We described above several features related to operator training. For example, instructional materials can be viewed on the medical equipment, as in a dedicated medical equipment training mode. Or, instructional materials can be viewed on a computer offering medical equipment specific training materials and instruction. Where training can be performed by in service medical equipment training modes, or, at a computer separate from the medical equipment, or by personal or group instruction, a medical equipment training record can record and indicate successful completion of needed training sessions or training modules by operator. On completion of a pre-determined training regimen, a particular operator can be added to an access list to perform certain access controlled operator functions on a type and/or model of medical equipment. The medical equipment can include operator training records or access training records on another computer, such as by a computer network to allow operator access by training qualification.

Evaluation of Operator Performance, "Inservice Error Monitoring":

Having described above several approaches to assist operators in the use and operation of medical equipment, we realize that the medical equipment alone probably cannot prevent every potential operator caused error. We also realize that there will probably remain situations such as where a highly dedicated and professional operator does not understand a remedial instruction as presented by the equipment. Also, some operators will probably continue to produce erroneous measurements without trying to understand why they are generating the errors. Such lack of concern for accuracy might be attributed to extreme fatigue or in a worst case, to a poor operator attitude.

Thus, we anticipate a need for feedback to both management and operators having multiple instances of operator requests for help and/or equipment detected difficulties with medical equipment. Medical equipment having some or all of the on demand and in service help features described herein can record instances of requests for help as well as equipment generated interventions. "In-service error monitoring" records can be created by time and location (e.g. by room or patient no.) and/or by operator identification. Alternatively, where an operator is not explicitly known to the equipment, overall hospital data collection records can typically be later cross referenced or compiled to associate medical equipment, for example, with a particular shift, room, clinical worker, and/or patient name or number. Such in-service error data reporting can also be handled completely anonymously as to particular operators so that an organization can identify common errors and discuss them, for example, in group training sessions or memos.

Exemplary areas for error monitoring include equipment maintenance issues as well as operator use issues with regard to making certain types of physiological measurements. For example, each individual unit of medical equipment can monitor how it is being recharged and whether it is receiving sufficient re-charge times.

As another operator use example, operator cycles can be recorded for measurements such as BP readings or $SpO_2$ readings taken during a pre-determined period of time. For example, in one embodiment, medical equipment can record instances of a physiological measurement made during a work shift, such as $SpO_2$ readings taken per patient. Records indicating that one particular operator takes significantly more readings per work shift (e.g. 25% more readings on rounds than an average group of operators on similar rounds) might show a problematic operator usage technique and therefore indicate a need for additional operator training. Where operator performance is recorded in a way that is traceable to a particular operator or to a small number of operators (e.g. a shift in a particular unit), specific training can be directed as needed to the individual operator or to a small group of individuals to address recurrence of specific types of operator errors. Supervisor or management feedback based on equipment reported operator errors can be entirely positive, such as "I noticed you have been having some troubles with the blood pressure alarms on the medical monitor in room . . . ", etc. In rare cases, where repeated operator errors appear to be caused by an operator having a complete lack of interest in learning proper use of equipment, a different type of behavioral intervention might be required, perhaps directed towards overall operator attitude or behavior rather than to a specific type of technical training assistance.

Equipment records of help requests and/or equipment offers of assistance, such as records created following equipment detected operator errors, can be stored in the equipment or automatically transmitted out, such as by wireless interface. For example, in some embodiments, following entry of a supervisor password, a supervisor can access records in the equipment at the medical equipment, using equipment generated on screen menus. Or in other embodiments having sufficient record or database access control, the medical equipment can transmit such records by a wireless connectivity, such as by WiFi to a computer on a network, such as to a computer on a hospital networked system. One or more computers designed to receive medical equipment operator performance records can generate summary reports by equipment type, hospital shift, and/or by operator identification. Management or supervisors can then review such reports and tailor training with a goal of minimizing certain types of reported confusion over equipment operation or modes of operation.

In service error monitoring can be maintained and viewed as tabulated data, such as in text listings that include relevant information such as the error type, time and date, room, patient number, and/or operator group or operator name. Similarly graphical trends can be plotted from the raw error data. Such tabulated data and/or graphical trending can be stored and presented on either the medical equipment and/or on a separate computer. A medical instrument can be configured to automatically send error information, such as by WiFi (e.g. an 802.11 network) to one or more computers on a network.

There can also be error threshold settings associated with in service error monitoring. For example, a medical manager can define error monitoring priorities, such as by error type. A certain number of errors, such as by a particular operator or group of operators can cause the medical equipment or a computer receiving in service error monitoring information from medical equipment to automatically trigger alerts, alarms, and/or to generate error reports.

Medical equipment, subject to compliance with privacy concerns, can also make reports back to a medical equipment manufacturer. Such reports can be used by a medical equipment manufacturer to identify, for example, large numbers of requests for assistance as related to a particular equipment mode or type of probe. Reports to manufacturers can be devoid of identifiers that might be construed as containing patient or operator identification to protect privacy concerns. Equipment manufacturers can respond to generic operator problem reports by providing additional training support, such as field assistance bulletins with regard to commonly detected operator problem areas, as well as to develop upgrades that can, for example, cause certain equipment modes or help screens to be more intuitive to an operator. In some embodiments, it is anticipated that a medical equipment manufacturer can "push" firmware upgrades, via wired or wireless networks, directly to the medical equipment, including for example, improved operator interfaces and improved operator help features responsive to received in service error monitoring reports.

Formats

Advice, operator procedure assistance, and other help can be offered by medical equipment to clinicians attempting to operate the medical equipment can be presented in many formats. In more basic embodiments, communications with the clinician can be via text messages on a display screen. Such text messages can be in characters matching equipment diagnostic readings or in bolder fonts, different fonts, blinking fonts, and can be accompanied by sounds, such as audio alarms. Moving text across a screen can also be used to draw attention to a message or to make a long message appear on a limited size screen. On slightly more sophisticated medical equipment having image capable displays, images can convey text, operating configurations, probe placement, or any combinations of such information. In medical equipment having a video compatible display, messages can appear as short movies or movie clips. For example, there can be an "in-service" video or movie "in the field" on how to operate the equipment, such as how to set up a particular mode of operation or how to place a certain type of physiological probe on the body or in a body cavity. Messages can also be conveyed to a clinician by audio, including text to speech routines running on a microcomputer in the medical equipment.

Definitions

We define "microcomputer" herein as synonymous with microprocessor, microcontroller, and digital signal processor ("DSP"). It is understood that memory used by the microcomputer, including for example medical equipment "firmware" can reside in memory physically inside of a microcomputer chip or in memory external to the microcomputer or in a combination of internal and external memory. Similarly, analog signals can be digitized by a stand alone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Medical equipment having any of the inventive features described herein can operate entirely on one microcomputer or can include more than one microcomputer.

We define medical equipment herein as synonymous with medical equipment system, medical instrument, medical monitor, and medical instrument. As defined herein, medical equipment, medical instruments, and medical monitors, can include electronic medical systems of varying complexity ranging from an electronic thermometer to a sophisticated medical monitor capable of simultaneously measuring a large number of physiological parameters.

While the present invention has been particularly shown and described with reference to the structure and methods disclosed herein and as illustrated in the drawings, it is not confined to the details set forth and this invention is intended to cover any modifications and changes as may come within the scope and spirit of the following claims.

What is claimed is:

1. A medical monitor comprising:
at least one physiological sensor, said at least one physiological sensor being configured to measure a physiological parameter;
an electronic circuit configured to receive a signal from said at least one physiological sensor, said electronic circuit further comprising a microcomputer programmed to process said signal from said at least one physiological sensor and to generate a value representative of said physiological parameter; and
a display connected to said electronic circuit,
said microcomputer being further programmed to cause said medical monitor to display an in-service help screen on said display in response to a detection of a predetermined number of out of range values of said physiological parameter,
said in- service help screen displaying at least one corrective measure for a user relating to said at least one physiological sensor,
said at least one corrective measure being provided in a non-textual form,
said microcomputer including a timer, the microcomputer being further programmed to initiate the timer when commencing a medical measurement using said at least one physiological sensor,
wherein said microcomputer is further programmed to determine whether a condition of said physiological sensor has been achieved within a predetermined time period and if said condition has not been achieved within said time period, then said microcomputer is programmed to display a corrective measure for a user and wherein said at least one physiological sensor comprises an oral temperature probe wherein said in-service help screen displays an image of a sublingual pocket indicating a correct placement of said oral temperature probe within said pocket to assist a user.

2. The medical monitor of claim 1, where said microcomputer is programmed with one or more instructions comprising an algorithm configured to determine whether said value representative of said physiological parameter is a value within a range of expected values.

3. The medical monitor of claim 1, where said microcomputer is programmed with one or more instructions comprising an algorithm configured to determine whether said value representative of said physiological parameter is a value outside a range of expected values.

4. The medical monitor of claim 1, wherein said at least one physiological sensor comprises a temperature probe type selected from the group of probe types consisting of an oral temperature probe, an axillary temperature probe, and a rectal temperature probe, wherein said microcomputer is further programmed upon said detection of a predetermined number of out of range values to determine a predetermined number of out of range values expected for the selected probe type, and in which said in-service help screen displays a warning that an improper probe type may have been selected for use, including a tutorial on how to implement the correct probe type based on said values.

5. The medical monitor of claim 1, wherein said at least one physiological sensor comprises an ECG assembly having a plurality of ECG leads configured to provide respiration measurements, wherein upon detection of a predetermined number of out of range values said microcomputer is further programmed to display a warning indicative of insufficient or anomalous respiration and an advisory message to check ECG lead placement and ECG lead types, including a displayed image depicting proper ECG lead placement.

6. The medical monitor of claim 1, wherein said at least one physiological sensor comprises a $SPO_2$ probe wherein detection of a predetermined number of out of range values is indicative of detection of anomalous $SPO_2$ levels.

7. The medical monitor of claim 6, wherein said in-service help screen on said display further displays a warning that a defective $SPO_2$ probe is suspected and a suggestion to replace said defective $SPO_2$ probe.

8. The medical monitor of claim 1, wherein said at least one physiological sensor comprises a $CO_2$ probe wherein detection of a predetermined number of out of range values is indicative of detection of abnormally low $CO_2$ levels and upon said detection, said microcomputer is further programmed to cause the in-service help screen to display a warning that an esophageal intubation is suspected and to display an image showing a proper intubation.

9. The medical monitor of claim 1, wherein said at least one physiological sensor comprises a capnography probe and upon said detection of a predetermined number of out of range values, said microcomputer is further programmed to display a warning that an air leak is suspected and at least a selected one of: an image of a endotracheal tube cuff, an image of a tracheal tube cuff, and an image of an artificial airway showing a problematic airflow possibly due to an insufficient opening.

10. The medical monitor of claim 1, wherein said at least one physiological sensor comprises a capnography probe wherein said detection of a predetermined number of out of range values comprises a detection of a slope of an ascending limb of a capnogram that has little or no alveolar plateau, and wherein said microcomputer is further programmed to display a warning including at least a selected error source including: a warning that an endotracheal tube kink is suspected, a warning that the patient airway is otherwise obstructed, and a recommendation for immediate intervention, each of said warnings including an image of said suspected error source.

11. The medical monitor of claim 10, wherein said in-service help screen further comprises suggestions of possible causes including at least a selected one of: suggestion if no visible kinks, consider bronchospasm, suggestion of COPD, suggestion of foreign body in the upper airway, and suggestion of herniated endotracheal or tracheal tube cuff, each of said suggestions being displayed by visual representations of same.

12. The medical monitor of claim 1, wherein said at least one physiological sensor comprises a capnography probe and said detection of a predetermined number of out of range values is indicative of detection of increasing $EtCO_2$ values, and a capnography shows an elevated baseline or a capnograph waveform does not return to zero at the end of inspiration.

13. The medical monitor of claim 12, wherein said in-service help screen on said display comprises a warning that $CO_2$ re-breathing is suspected and a suggestion that an operator look for at least a selected one of the following potential error sources: suggestion of an inadequate expiratory time, suggestion of a malfunctioning inspiratory valve, suggestion of an insufficient inspiratory flow rate, and suggestion of a malfunction in the breathing circuit, said in-service help screen providing visual representations of each of said suggested potential error sources.

14. The medical monitor of claim 1, wherein said at least one physiological sensor comprises a temperature probe type selected from the group of probe types consisting of an oral temperature probe, an axillary temperature probe and a rectal temperature probe in which detection of a predetermined number of out of range values is indicative of detection of a temperature measurement beyond a pre-determined temperature, and upon said detection said microcomputer is further programmed to automatically display an instruction to an operator to order at least one pre-determined type of lab work based on said temperature measurement.

15. The medical monitor of claim 1, wherein said corrective measure includes an assistance image of said at least one physiological sensor as properly configured for measurement relative to a patient.

16. The medical monitor of claim 15, wherein said microprocessor is further programmed to initiate said the timer upon the removal of said physiological sensor from a stored position.

17. The medical monitor of claim 16, wherein said microprocessor is further programmed to initiate said the timer based upon removal of a temperature probe from a temperature probe storage well.

18. A medical monitor comprising:
an oral temperature probe, said oral temperature probe including a temperature measuring sensor;
an electronic circuit configured to receive a signal from said temperature measuring sensor, said electronic circuit further comprising a microcomputer programmed to process said signal from said temperature measuring sensor and to generate a value representative of patient body temperature; and
a display connected to said electronic circuit, said microcomputer being further programmed to cause said display to display temperature values generated by said microcomputer, said temperature probe being enabled when removed from a temperature probe storage well, said microcomputer including a timer, the microcomputer being programmed to initiate the timer when said temperature probe is removed from said storage well wherein the failure of said probe to generate threshold values within a predetermined time period causes said microcomputer to generate a corrective measure on said display to assist a user, said corrective measure including an image of a correctly positioned oral temperature probe within the sublingual pocket.

19. A method for configuring a medical monitor to provide assistance to a user of said monitor, said monitor including at least one physiological sensor coupled to an electronic circuit having a microprocessor and a display, said method comprising the steps of:
coupling said microprocessor and electronic circuit relative to said at least one physiological sensor to enable receipt of a signal from said at least one physiological sensor;
programming said microprocessor to process said signal and to generate a value representative of a measured physiological parameter for display by said monitor;
programming said microprocessor to automatically initiate timer upon enablement of said at least one physiological sensor;

programming said microprocessor to determine whether a specified condition occurs before the completion of a predetermined time period as measured by the timer; and if said specified condition has not occurred, then programming said microprocessor to display a corrective measure to the user, wherein said at least one physiological sensor comprises an oral temperature probe and in which said corrective measure is a displayed image of a sublingual pocket further displaying the correct placement of the oral temperature probe within said pocket to assist the user.

20. The method of claim 19, wherein said at least one physiological sensor is a temperature probe type selected from a group of probe types consisting of an oral temperature probe, an axillary temperature probe and a rectal temperature probe, and in which said microcomputer is programmed to automatically initiate the timer when said temperature probe has been removed from a probe storage well of said monitor.

21. The method of claim 20, wherein said microcomputer is programmed to determine whether threshold output signals have been received from said temperature probe during said predetermined time period indicative that the probe has been properly positioned on a patient and in which said displayed corrective measure includes an image of a correctly positioned temperature probe.

22. The method of claim 19, in which said at least one physiological sensor is an $SpO_2$ probe and in which said timer is initiated upon placement of said probe onto the finger of a patient, wherein the specified condition is the cessation of signals from the $SpO_2$ probe, indicating the probe is no longer on the finger of the patient and wherein the detection of signals from said probe after the completion of said predetermined period is indicative of potential injury to a patient, the corrective measure including a warning message suggesting the $SpO_2$ probe be moved to another site.

* * * * *